US011345599B2

(12) United States Patent
Yu et al.

(10) Patent No.: US 11,345,599 B2
(45) Date of Patent: May 31, 2022

(54) COMPOSITION, PARTICULATE MATERIALS AND METHODS FOR MAKING PARTICULATE MATERIALS

(71) Applicant: THE UNIVERSITY OF QUEENSLAND, St Lucia (AU)

(72) Inventors: Chengzhong Yu, Prisbane (AU); Meihua Yu, Prisbane (AU); Hongwei Zhang, Prisbane (AU); Yusilawati Ahmad Nor, Prisbane (AU); Hao Song, Prisbane (AU)

(73) Assignee: THE UNIVERSITY OF QUEENSLAND, St Lucia (AU)

( * ) Notice: Subject to any disclaimer, the term of this patent is extended or adjusted under 35 U.S.C. 154(b) by 0 days.

(21) Appl. No.: 15/567,249

(22) PCT Filed: Apr. 18, 2016

(86) PCT No.: PCT/AU2016/050283
§ 371 (c)(1),
(2) Date: Oct. 17, 2017

(87) PCT Pub. No.: WO2016/164987
PCT Pub. Date: Oct. 20, 2016

(65) Prior Publication Data

US 2018/0105422 A1 Apr. 19, 2018

(30) Foreign Application Priority Data

Apr. 17, 2015 (AU) ................................ 2015901379

(51) Int. Cl.
| | |
|---|---|
| *C01B 33/12* | (2006.01) |
| *C01B 32/15* | (2017.01) |
| *C01B 33/18* | (2006.01) |
| *A61K 9/51* | (2006.01) |
| *B01J 20/32* | (2006.01) |
| *B01J 20/28* | (2006.01) |
| *B82Y 30/00* | (2011.01) |
| *B82Y 40/00* | (2011.01) |
| *B01J 20/10* | (2006.01) |
| *H01M 4/62* | (2006.01) |
| *B01J 13/18* | (2006.01) |
| *B01J 13/20* | (2006.01) |
| *A01N 25/28* | (2006.01) |
| *H01M 4/58* | (2010.01) |
| *H01M 4/66* | (2006.01) |
| *B82Y 5/00* | (2011.01) |
| *H01M 4/134* | (2010.01) |

(52) U.S. Cl.

CPC .............. *C01B 32/15* (2017.08); *A01N 25/28* (2013.01); *A61K 9/5115* (2013.01); *B01J 13/18* (2013.01); *B01J 13/20* (2013.01); *B01J 13/203* (2013.01); *B01J 20/10* (2013.01); *B01J 20/28007* (2013.01); *B01J 20/28021* (2013.01); *B01J 20/28057* (2013.01); *B01J 20/3293* (2013.01); *B82Y 30/00* (2013.01); *B82Y 40/00* (2013.01); *C01B 33/18* (2013.01); *H01M 4/5815* (2013.01); *H01M 4/625* (2013.01); *H01M 4/663* (2013.01); *B82Y 5/00* (2013.01); *C01P 2004/34* (2013.01); *C01P 2004/61* (2013.01); *C01P 2004/62* (2013.01); *C01P 2006/16* (2013.01); *H01M 4/134* (2013.01)

(58) Field of Classification Search
None
See application file for complete search history.

(56) References Cited

U.S. PATENT DOCUMENTS

| | | | | |
|---|---|---|---|---|
| 2002/0064541 | A1 | 5/2002 | Lapidot et al. | |
| 2003/0157330 | A1 | 8/2003 | Ostafin et al. | |
| 2005/0244322 | A1 * | 11/2005 | Chen | C01B 37/02 423/335 |
| 2006/0118158 | A1 * | 6/2006 | Zhang | H01L 35/34 136/205 |
| 2008/0317795 | A1 | 12/2008 | Traynor et al. | |
| 2009/0136816 | A1 | 5/2009 | Kang et al. | |

(Continued)

FOREIGN PATENT DOCUMENTS

| | | | |
|---|---|---|---|
| CN | 101058824 | A | 10/2007 |
| CN | 101391776 | A | 3/2009 |

(Continued)

OTHER PUBLICATIONS

XU et al.; "Rod-like mesoporous silica nanoparticles with rough surfaces for enhanced cellular delivery," 2014, RCS; Journal of Materials Chemistry B, vol. 2, pp. 253-256. (Year: 2014).*
XU; "Rod-like mesoporous silica nanoparticles with rough surfaces for enhanced cellular delivery," RSC, Journal of Material Chemistry B, 2014, No. 2, pp. 253-256; first published on Nov. 11, 2013. (Year: 2013).*
Grumezescu et al.; "New Silica nanostructure for the improved delivery of topical antibiotics used in the treatment of staphylococcal cutanous infection," 2014; Elsevier; International Journal of Pharmaceutics, vol. 463, pp. 170-176. (Year: 2014).*

(Continued)

*Primary Examiner* — David J Blanchard
*Assistant Examiner* — Ivan A Greene
(74) *Attorney, Agent, or Firm* — Nixon & Vanderhye P.C.

(57) ABSTRACT

Particulate material comprising rough mesoporous hollow nanoparticles. The rough mesoporous hollow nanoparticles may comprise a mesoporous shell, the external surface of which has projections thereon, the projections having smaller sizes than the particle size. The particulate material may be used to deliver active agents, such as insecticides and pesticides. The active agents can enter into the hollow core of the particles and be protected from degradation by sunlight. The rough surface of the particles retains the particles on plant leaves or animal hair. Methods for forming the particles are also described. Carbon particles and methods for forming carbon particles are also described.

31 Claims, 14 Drawing Sheets

(56) References Cited

U.S. PATENT DOCUMENTS

| | | | |
|---|---|---|---|
| 2010/0264097 A1* | 10/2010 | Sun | B01J 35/1076 210/767 |
| 2011/0177951 A1 | 7/2011 | Toledano et al. | |
| 2011/0230343 A1 | 9/2011 | Schroers et al. | |
| 2012/0172213 A1 | 7/2012 | Ghoi et al. | |
| 2013/0230570 A1 | 9/2013 | Trogler et al. | |
| 2013/0251773 A1* | 9/2013 | Galiatsatos | A01N 25/18 424/403 |
| 2013/0289520 A1* | 10/2013 | Febvay | A61K 41/0057 604/501 |

FOREIGN PATENT DOCUMENTS

| | | |
|---|---|---|
| CN | 101708853 A | 5/2010 |
| CN | 102437318 A | 5/2012 |
| CN | 102580681 A | 7/2012 |
| CN | 104445214 A | 3/2015 |
| JP | 2003534249 A | 11/2003 |
| JP | 2009132607 A | 6/2009 |
| JP | 2010528990 A | 8/2010 |
| JP | 2011529392 A | 12/2011 |
| JP | 2012508090 A | 4/2012 |
| JP | 2013082599 A | 5/2013 |
| WO | WO-2013007354 A1 * | 1/2013 ............ A01N 25/34 |

OTHER PUBLICATIONS

Polshettiwar et al.; "High-Surface-Area Silica Nanospheres (KCC-1) with a Fibrous Morphology," 2010; Wiley-VCH; Angewandte Chemie International Edition vol. 49, No. 50, pp. 9652-9656. (Year: 2010).*

Chen F. et al.; "Engineering of Hollow Mesoporous Silica Nanoparticles for Remarkable Enhanced Tumor Active Targeting Efficacy," 2014; Scientific Reports, 4(5080), pp. 1-10. (Year: 2014).*

Wang et al.; "Budded, Mesoporous Silica Hollow Spheres: Hierarchial Structure Controlled by Kinetic Self-Assembly," 2006, Wiley-VCH; Advanced Materials, vol. 18, pp. 3284-3288. (Year: 2006).*

Chen F. et al.; "Engineering of Hollow Mesoporous Silica Nanoparticles for Remarkably Enhanced Tumor Activity Targeting Efficacy," 2014; Scientific Reports, 4(5080), pp. 1-10. (Year: 2014).*

Grumezescu et al.; "New Silica nanostructure for the improved delivery of topical antibiotics used in the treatment of staphylococcal cutaneous infection," 2014; Elsevier; International Journal of Pharmaceutics, vol. 463, pp. 170-176. (Year: 2014).*

Xia et al.; "Polyethyleneimine Coating Enhances the Cellular Uptake of Mesoporous Silica Nanoparticles and Allows Safe Delivery of siRNA and DNA Constructs," 2009; ASCNano, vol. 3, No. 10, pp. 3273-3286. (Year: 2009).*

Yang et al.; "Synthesis of hollow spheres with mesoporous silica nanoparticles shell," 2008, Elsevier; Materials Chemistry and Physics, vol. 111, pp. 5-8. (Year: 2008).*

International Search Report for PCT/AU2016/050283 dated Jun. 20, 2016, 6 pages.

Written Opinion of the ISA for PCT/AU2016/050283, dated Jun. 20, 2016, 11 pages.

Xu et al.: "Rod-like mesoporous silica nanoparticles with rough surfaces for enhanced cellular delivery" Journal of Materials Chemistry B, 2014, No. 2, pp. 253-256.

Chen et al.: "Engineering of Hollow Mesoporous Silica Nanoparticles for Remarkably Enhanced Tumor Active Targeting Efficacy" Scientific Reports, 2014, vol. 4, No. 5080, [online] < http://www.nature.com/articles/srep05080 > [retrieved on May 20, 2016].

Nor et al.: "Shaping Nanoparticles with Hydrophilic Compositions and Hydrophobic Properties as Nanocamers for Antibiotic Delivery" ACS Central Science, Sep. 2015, No. 1, pp. 328-334.

Niu et al.: "Nanoparticles Mimicking Viral Surface Topography for Enhanced Cellular Delivery" Advanced Materials, 2013, vol. 25, issue 43, pp. 6233-6237.

Qiao et al.: "Synthesis of Mesoporous Silica Nanoparticles via Controlled Hydrolysis and Condensation of Silicon Alkoxide" Chemistry of Materials, 2009, vol. 21, No. 16, pp. 3823-3829.

Langmuir 199, J, Colloid Interface Science, 2008, 317:442.

Wang, Meng, et al., "Application of tailored silica microspheres in coatings: synthesis, characterization, thermal and hydrophobic properties," Journal of Materials Chemistry A, vol. 1, No. 37, 2013, pp. 11465-11472, XP055514949.

Xu, Chun, et al., "Core-Cone Structured Monodispersed Mesoporous Silica Nanoparticles with Ultra-large Cavity for Protein Delivery," Small 2015, vol. 11, No. 44, pp. 5949-5955.

Yue, Qin, et al., "An Interface Coassembly in Biliquid Phase: Toward Core-Shell Magnetic Mesoporous Silica Microspheres with Tunable Pore Size," Journal of the American Chemical Society 2015, vol. 137, pp. 13282-13289.

English translation of Notice of Reasons for Rejection dated Mar. 10, 2020, issued in Japanese Patent Application No. 2017-550594, 9 pages.

Liu, Hui, et al., "Preparation of Porous Hollow SiO2 Spheres by a Modified Stober Process Using MF Microspheres as Templates," Journal of Cluster Science, 2011, vol. 23, pp. 273-285.

Xu, Chun, et al., "Rod-like mesoporous silica nanoparticles with rough surfaces for enhanced cellular delivery," Journal of Materials Chemistry B, 2014, vol. 2, pp. 253-256.

The identified references were cited in a Chinese examination report.

Wang, Meng, et al., "Application of tailored silica microspheres in coatings: synthesis, characterization, thermal and hydrophobic properties," Journal of Materials Chemistry A, vol. 1, No. 37, 2013, p. 11465-11472, XP055514949.

Xu, Shuping, et al., "Increasing Surface Area of Silica Nanoparticles With a Rough Surface," ACS Applied Materials & Interfaces, vol. 3, No. 6, 2011, pp. 1865-1872, XP055514844.

Extended European Search Report dated May 7, 2020, issued in European Patent Application No. 20153055.7, 8 pages.

* cited by examiner

COMPOSITION, PARTICULATE MATERIALS AND METHODS FOR MAKING PARTICULATE MATERIALS

This application is the U.S. national phase of International Application No. PCT/AU2016/050283 filed 18 Apr. 2016, which designated the U.S. and claims priority to AU Patent Application No. 2015901379 filed 17 Apr. 2015, the entire contents of each of which are hereby incorporated by reference.

TECHNICAL FIELD

The present invention relates to particulate materials and to methods for forming particulate materials. The present invention also relates to a composition. The present invention also relates to a composition containing hydrophobic compounds; and/or a composition with hydrophobic properties. Some of the particulate material may be used in compositions in accordance with aspects of the invention.

BACKGROUND ART

Australia is among the world's largest and most successful producers of commercial livestock, which contributes ~1% to Australian's gross domestic product (GDP). The export of red meat and livestock contributed a total value of ~$16 billion in 2012-2013. However, arthropod pests pose a serious threat to the industry. It is estimated that ticks cost the cattle industry around $170-200 million each year. Furthermore, buffalo fly and sheep lice infestations have caused millions of dollars in losses due to the cost of implementing control strategies and lost productivity. The high cost of ectoparasite treatment is primarily due to the high dose rates and repeated treatments of active compounds required to achieve efficacy. Moreover, many pesticides currently in use have high toxicity, negative environmental effects and potential risks to human health and food safety. Arthropod pests are equally threatening to plant crops such as cereals, vegetables and fruit.

Spinosad is a naturally derived pesticide with low environmental impact and low mammalian toxicity. However, its use is currently limited in part by its UV instability which reduces potency, low water solubility and hydrophobicity, making formulation in aqueous systems difficult and higher cost relative to conventional chemical pesticides. Spinosad is currently registered for use in sheep to treat lice and fly infestations, however, its reduced potency and duration of efficacy against ectoparasites of cattle has prevented its registration as a treatment for buffalo fly and cattle tick. Likewise, these drawbacks have limited Spinosad's use in crop protection applications where aqueous formulations are commonly used and UV stability is required by pesticides that reside on plant surfaces following application.

Many other compounds that are used as insecticides or pesticides are also hydrophobic. As a result, if a water-based composition is to be used for application of those insecticidal pesticides, a suspension or emulsion will typically be required. Suspensions or emulsions can suffer from short shelf life, due to a tendency to separate into separate layers. Application via spraying can also be difficult for the same reason. Further difficulties are encountered if the compounds are sensitive to light or ultraviolet light. In such circumstances, the compounds can have a short period of effectiveness following application due to the compound breaking down when exposed to sunlight.

A number of other hydrophobic compounds have beneficial effects when used in biological systems. These compounds may include compounds having a therapeutic effect on an animal or human (such as an antibiotic, cancer drug or other drug for treating disease), proteins and dyes for use as marker agents. Delivery of such agents to biological systems can be difficult.

In biological systems, hydrophobic interactions are usually considered to be the strongest of all long-range non-covalent interactions. Hydrophobic interaction is beneficial for adsorption of biomolecules, improving interaction with cellular membranes increasing the uptake of nanoparticles for cellular delivery as well as tailoring the release rate of drugs. To generate nanoparticles with hydrophobic properties, the choices of hydrophobic composition or functionalization are among the convenient approaches. Hydrophobic material such as carbon nanotubes (CNTs) have shown great promise as nanoscaled vehicles for drug delivery, however one of the main concerns is the fact that CNTs could be hazardous to environmental and human health, requiring further surface functionalization to reduce their intrinsic toxicity. Hydrophobic moieties such as alkanethiols and alkyl chains have been used to modify the surfaces of various nanoparticles including gold and silica to enhance the loading of hydrophobic drugs/protein and improve cellular delivery performance. However, chemically grafted hydrophobic groups tended to cause unwanted toxicity and pore blocking of nano-carriers. It is therefore a challenge to design a safe and efficient hydrophobic nanocarrier system employing an alternative approach.

In addition to difficulties encountered in formulating hydrophobic agents, many active molecules aside from Spinosad that are used as drugs, insecticides or otherwise suffer from limited active lifetime in the field due to UV degradation. This is especially the case for active molecules that are applied topically and therefore are more likely to be exposed to UV light including topical formulations used for humans and animals and those used in crop protection. The ability to formulate these active molecules into a UV protecting carrier system could enable longer duration of effectiveness.

Of course, there is little value in extending the duration of action of an active molecule by protecting it against UV light if other factors, such as wash-off of the active molecule from the site of action, occur before the active molecule can take full effect. In many applications including the topical application of active molecules and in crop protection, wash-off of active molecules by rain, wind abrasion and other erosive forces can significantly reduce the efficacy and duration of action of an active molecule.

In gene therapy, remarkable therapeutic benefits in the treatment of diseases caused by genetic disorders, where the efficacy of the delivery vehicles is the key to introducing nucleic acids into cells to achieve their functions has been demonstrated. DNA vaccination is a most recent form of treatment, where a plasmid DNA (p-DNA) encoding an antigen of interest is delivered into cells to induce antigen-specific immunity. Here, rather than injecting a patient with a vaccine antigen as is commonly done in the cases of vaccination using sub-unit vaccines, patients are injected with p-DNA molecules that provide the body's cells with the code to produce the antigen in vivo, effectively allowing the body to produce its own antigen. Vaccination strategies using other nucleic acid forms such as messenger RNA (mRNA) are also emerging.

Effective delivery of the p-DNA into target cells has been a significant challenge for this promising approach. DNA vaccines are promising vaccine candidates as they are very specific, safe and well tolerated and relatively inexpensive to manufacture. However poor immunogenicity is a major problem and a significant cause of this is the inability of the p-DNA to be effectively delivered to the cell nucleus so that the DNA can be incorporated to then produce the vaccine antigen. Inefficient delivery of p-DNA is caused by three main factors, all of which combined mean that only a small proportion of p-DNA injected into the body actually makes it into the cell nucleus to enable the production of vaccine antigens:
1. Breakdown of the p-DNA by nucleases after injection or delivery into the body and before the p-DNA enters the cell
2. Inability to be efficiently transported across the cell membrane into the cell
3. Inability to efficiently enter the cell nucleus once inside the cell Delivery of p-DNA using viral delivery systems (one of the first delivery systems to be investigated) proved to be effective in delivering p-DNA to the cell however toxicity problems have reduce the promise of these earlier delivery system candidates. Since then, polymer microspheres and cationic liposomes have emerged as two promising new delivery technologies, although neither likely is good enough to allow DNA vaccines to be widely adopted.

Cationic liposomes are able to load reasonable quantities of p-DNA and loading is easy so that the p-DNA is not damaged during the process. Protection against nucleases is good since the p-DNA can be encapsulated within the liposome. However the liposomes are soft particles and so are not very stable in vivo. Toxicity is also of great concern. Polymer microparticles are also used as a carrier for p-DNA. The polymers are typically more rigid than liposomes so do not have the tendency to mechanically degrade in vivo. Polymer microparticles also provide good protection for the p-DNA against nucleases. However the key polymers that have been proposed (polylactic acid and poly(lactic-co-glycolic acid)) form hydrophobic particles and are negatively charged and so may not properly encapsulate the p-DNA. In addition, the loading methods are generally quite harsh, which may damage the p-DNA during processing. Transfection efficiency tends to be low. Polyethylenimine (PEI) has been shown to enable higher transfection efficiencies however these polymers can be extremely cytotoxic. Understanding the unique loop structure of p-DNA molecules and rational design of advanced p-DNA delivery vehicles is highly desired for efficient gene therapy and DNA vaccination strategies.

It will be clearly understood that, if a prior art publication is referred to herein, this reference does not constitute an admission that the publication forms part of the common general knowledge in the art in Australia or in any other country.

SUMMARY OF INVENTION

The present invention is directed to a composition that includes one or more hydrophobic compounds; and/or a nanostructure that has hydrophobic properties. In other aspects of the present invention, particulate material and methods for forming particulate material are provided.

In a first aspect, the present invention provides particulate material comprising rough mesoporous hollow nanoparticles.

Rough mesoporous hollow nanoparticles are defined as hollow particles or spheres with a mesoporous shell, the external surface of which has projections thereon, the projections having smaller sizes than the particle size. The particle size may range from 100 nm to 3000 nm, the size of projections may range from 5 nm to 1000 nm, preferably from 100 nm to 500 nm. In one embodiment, the projections may comprise nanospheres on the shell.

In one embodiment, the mesoporous shell may comprise, silica, Ag, Au, calcium phosphate or titanium dioxide or carbon or a carbon-based material. In one embodiment, the rough mesoporous hollow nanoparticles comprise rough mesoporous hollow silica nanoparticles.

In one embodiment, the particles are made from a material that is normally hydrophilic but the particles demonstrate hydrophobic characteristics.

The rough mesoporous hollow nanoparticles will typically have a hollow core that is surrounded by a shell having a mesoporous structure. As the shell that surrounds and defines the hollow core is porous, compounds may pass through the pores and enter into the hollow core. Projections which may have spherical or other shapes are present on the outside of the shell, providing a rough surface to the particles. Although the material from which the rough mesoporous hollow nanoparticles (such as silica) may normally be a hydrophilic material, the rough surface results in the rough mesoporous hollow nanoparticles exhibiting hydrophobic properties, thereby allowing or even enhancing movement of the hydrophobic compounds into the hollow core.

The rough mesoporous hollow nanoparticles will typically have a hollow core having a diameter of from 100 nm to 1000 nm, or from 100 nm to 700 nm. The hollow core will be defined by a shell, such as a shell of silica in the case of rough mesoporous hollow silica nanoparticles, having a mesoporous structure. The shell (such as the shell of silica) will typically have a pore structure that includes pores in the range of from 2 nm to 20 nm. As the shell that surrounds and defines the hollow core is porous, compounds may pass through the pores and enter into the hollow core. The shell that surrounds the hollow core may have a thickness of from 10 nm to 100 nm. The rough mesoporous hollow nanoparticles may include projections or outgrowths on the surface, spaced apart from each other. The spaced projections or outgrowths provide surface roughness to the particles. The surface roughness is sufficient to result in the rough mesoporous hollow nanoparticles taking on a hydrophobic character, in some cases extremely hydrophobic.

In embodiments where the rough mesoporous hollow nanoparticles comprise rough mesoporous hollow silica nanoparticles, the rough mesoporous hollow silica nanoparticles will typically have a hollow core having a diameter of from 100 nm to 1000 nm, or from 100 nm to 700 nm. The hollow core will be defined by a silica shell having a mesoporous structure. The silica shell will typically have a pore structure that includes pores in the range of from 2 nm to 20 nm. As the silica shell that surrounds and defines the hollow core is porous, compounds may pass through the pores and enter into the hollow core. The silica shell that surrounds the hollow core may have a thickness of from 10 nm to 100 nm. The rough mesoporous hollow silica nanoparticles may include silica projections or outgrowths on the surface, spaced apart from each other. The spaced silica projections or outgrowths provide surface roughness to the particles. The surface roughness is sufficient to result in the rough mesoporous hollow silica nanoparticles taking on a hydrophobic character, in some cases extremely hydrophobic.

The spaced projections may comprise nanoparticles connected to the outer surface of the larger hollow nanoparticle.

The nanoparticles connected to the outer surface of the larger hollow nanoparticles may be of the same composition as the larger hollow nanoparticles or of a different composition to the larger hollow nanoparticles. The nanoparticles used to construct the projections may have a diameter in the range of from 5 nm to 100 nm and the hollow nanoparticles may have a diameter in the range of from 100 nm to 1000 nm. Alternatively, the spaced silica projections may comprise strands or cylinders or fibres or nodules extending outwardly from the hollow shell of the nanoparticles. The length of the projections may be from 5 nm up to the diameter of the large hollow particle on which they reside, however they may be made longer if required by the application. The diameter of the projections may be as low as 2-3 nm or as high as 100 nm or higher and the diameter or thickness of a projection may vary along its length due to the process used to form it. The specific surface area of the nanoparticles may range from 100 $m^2/g$ to 1000 $m^2/g$, or from 150 $m^2/g$ to 1000 $m^2/g$, or from 175 $m^2/g$ to 1000 $m^2/g$.

In embodiments where the rough mesoporous hollow nanoparticles comprise rough mesoporous hollow silica nanoparticles, the rough mesoporous hollow silica nanoparticles, the spaced projections or outgrowths suitably comprise silica projections or outgrowths. The spaced projections of silica may comprise silica nanoparticles connected to the outer surface of a larger hollow silica nanoparticle. The silica nanoparticles used to construct the projections may have a diameter in the range of from 5 nm to 100 nm and the hollow silica nanoparticles may have a diameter in the range of from 100 nm to 1000 nm. Alternatively, the spaced silica projections may comprise strands or cylinders or fibres or nodules of silica extending outwardly from the hollow silica nanoparticles. The length of the projections may be from 5 nm up to the diameter of the large hollow particle on which they reside, however they may be made longer if required by the application. The diameter of the projections may be as low as 2-3 nm or as high as 100 nm or higher and the diameter or thickness of a projection may vary along its length due to the process used to form it. The specific surface area of the nanoparticles may range from 100 $m^2/g$ to 1000 $m^2/g$, or from 150 $m^2/g$ to 1000 $m^2/g$, or from 175 $m^2/g$ to 1000 $m^2/g$.

In other embodiments, the rough mesoporous hollow nanoparticles comprise rough mesoporous hollow carbon nanoparticles.

In a second aspect, the present invention provides a composition comprising rough mesoporous hollow nanoparticles having one or more hydrophobic materials therein or thereon.

In one embodiment of the second aspect of the present invention, the hydrophobic material comprises an insecticide or a pesticide. In a preferred embodiment, the hydrophobic material comprises Spinosad. The hydrophobic material may be distributed throughout the particle, in the inner core, within the pores of the shell and/or on the surface of the porous shell and in between and on the projections, or any combination of these.

As mentioned above, Spinosad is very hydrophobic, has low water solubility and is extremely susceptible to degradation by exposure to UV light (such as occurs when exposed to sunlight). As a result, Spinosad has not found widespread use for treating ectoparasites and insect infestations in livestock (such as cattle and sheep) and plants by applying a composition containing Spinosad externally to the animal or the plant. The present inventors have surprisingly found that rough mesoporous hollow nanoparticles, such as rough mesoporous hollow silica nanoparticles, can take up Spinosad and other hydrophobic molecules in a manner that protects the hydrophobic molecules against UV light degradation, thereby enhancing photo stability and the duration of insecticidal activity. Moreover, the hollow core of the rough mesoporous hollow nanoparticles facilitates a high loading of Spinosad or other hydrophobic molecules in the particles, allowing commercially relevant formulations to be developed. In addition, the hollow and rough surface morphology of the rough mesoporous hollow nanoparticles increases the hydrophobicity of the particles and further enhances Spinosad loading capacity. The rough mesoporous hollow nanoparticles have also been found to adhere more strongly to skin, hair and other surfaces such as the leaves of plants, thus further prolonging the duration of insecticidal activity of Spinosad under field conditions. The rough mesoporous hollow nanoparticles are likely to adhere more strongly to leaves of plants, particularly leaves that have hairs on them. This improved adhesion further enhances the potency and longevity of the insecticide by minimising wash-off of the insecticide residues following application. Consequently, more environmentally friendly formulations where a lower label dose is used may be feasible with the present invention.

The present invention is not limited to compatibility with any particular class of hydrophobic molecule, and as such, may be used with a wide range of hydrophobic molecules. Other hydrophobic pesticides that may be formulated with the particles of the present invention include, but are not limited to pyrethroid, azadirachtin (neem oil) and pyrethrum. Similar to Spinosad, these are natural products which are safe to use but breakdown quickly under sunlight. Indeed, many new pharmaceutically active molecules currently under development suffer from problems of hydrophobicity or UV degradation and these are likely to be compatible with the particles of the present invention.

In one embodiment, the present invention provides an insecticidal composition for external application to an animal or plant, the composition comprising rough mesoporous hollow nanoparticles having one or more hydrophobic insecticidal materials therein. In one embodiment, the rough mesoporous hollow nanoparticles comprise rough mesoporous hollow silica nanoparticles.

The one or more hydrophobic materials will suitably be present in the hollow core of the nanoparticles. The one or more hydrophobic materials are also likely to be present in the spaces between raised or projecting regions that produce the surface roughness of the nanoparticles.

The rough mesoporous hollow nanoparticles can also be used as efficient vehicles for delivery of hydrophobic material to biological systems, such as drug delivery of hydrophobic drugs, carriers and delivery agents for hydrophobic proteins and as carriers and delivery agents for hydrophobic dyes that can be used as marker agents. The rough mesoporous hollow nanoparticles after further modification with hydrophobic compounds to yield superhydrophobic particles can be employed in the removal of water pollutants and in surface coatings for self-cleaning applications. Methods for hydrophobic modification of surfaces such as silica including the covalent attachment of moieties containing hydrophobic groups using silanes and other agents are well-known to those skilled in the art.

In one embodiment, the hydrophobic material may comprise a hydrophobic protein, such as RNase A, insulin or lysozyme, a hydrophobic dye, such as disperse red 1, solvent red or rose bengal, a hydrophobic drug or therapeutic agent, such as griseofluvin, curcumin, ibuprofen or erythromycin or vancomycin or an essential oil such as oregano oil. In the case of essential oils, the present invention can provide a means for increasing the solubility of the hydrophobic essential oils, making them more bioavailable and therefore enabling dose sparing strategies to minimise essential oil costs in the manufacture of formulations. Essential oils are also known to be relatively volatile compounds and significant amounts of oil can be lost to evaporation during the manufacture, storage and use of essential oil formulations. By loading the essential oils into the particles of the present invention, losses to evaporation can be minimised and essential oils costs in manufacturing a formulation can be reduced without negatively affecting the efficacy of the product. Lysozyme and other enzymes that are used in cosmetics, animal feed supplements and other applications may also be formulated with the particles of the present invention. Here, the particles can provide a slow release function, which in the case of lysozyme for example which has antibacterial properties, can result in sustained suppression of bacteria over time. During the manufacture and storage of enzyme formulations, many enzymes suffer degradation as a result of thermal breakdown, hydrolysis or otherwise, requiring excess enzyme to be used in formulations in order to compensate for these yield losses. For example, in the steam pelleting process used to make some animal feeds, the application of steam can result in denaturation of some of the enzyme content, requiring either excess enzyme to be added to the formulation or the use of expensive equipment to spray enzyme onto the resulting pellets following the steam pelleting process. Formulation of enzymes with the particles of the present invention can protect the enzyme from degradation. These active ingredients may be loaded into the internal cavity provided by the particles, on the outside of the particles entangled with the projections or a combination of both. How the active ingredient is distributed between the internal cavity and external surface depends of the desired rate of release, the size of the molecule, the desired loading level, the extent of protection needed by the active ingredient and other factors.

Without wishing to be bound by theory, the present inventors have postulated that active molecules may adsorb onto the surface of the particles or be inserted into the voids between the projections on the particles and this provides a degree of protection against degradation of the active materials, even if the active materials do not enter (partially or completely) into the hollow core of the particles.

The present inventors have also found that rough mesoporous hollow nanoparticles can be used to provide for sustained release of compounds taken up therein. Accordingly, in a third aspect, the present invention provides a composition for providing sustained release of a compound, the composition comprising rough mesoporous hollow nanoparticles having compounds taken up therein. In this aspect, the compound may be a hydrophobic compound or may be a hydrophilic compound. The compound may comprise any of the materials described as being suitable for use in the first aspect of the present invention. The compound may be a therapeutic agent, such as an antibiotic. The antibiotic may be, for example, vancomycin or metronidazole.

In other aspect, compatibility of the present invention is not limited to use with hydrophobic molecules. Many hydrophilic molecules could benefit from advantages provided by the particles of the present invention such as slow release, protection against UV degradation and enhanced adhesion to plant, animal or other surfaces.

Accordingly, in a fourth aspect, the present invention provides a composition comprising rough mesoporous hollow nanoparticles having one or more hydrophilic materials therein.

In a fifth aspect, the present invention may also relate to a composition comprising rough mesoporous hollow nanoparticles having one or more active molecules therein or thereon. In some embodiments, the active molecules may be any of the active molecules described herein.

The present inventors have also found that the particles of the present invention can function as an effective delivery system for nucleic acids such as plasmid DNA (p-DNA) and messenger RNA (mRNA) that are used in emerging vaccination strategies. In the case of p-DNA, it is desirable to be able to protect the p-DNA molecule from attack by nucleases on entry of the p-DNA into the body. This mode of degradation of p-DNA is responsible for a significant reduction in the efficacy of DNA vaccines. Due to the large size of the p-DNA molecules, when formulated with the particles of the present invention p-DNA is largely distributed on the outside of the particles, secured by the projections on the surface of the particles. This is sufficient to provide a high degree of protection against attack by nucleases. In formulating a DNA or mRNA-based vaccine, the particles of the present invention may be coated with substances that increase the affinity of the particles to these nucleic acids. This may involve covalently grafting chemical functional groups onto the particles, or applying a coating that interacts with the particle surface via hydrogen bonding, electrostatic attraction or some other means known to those skilled in the art. For example, polyethylenimine (PEI) may be coated onto the particles. With a formulation substantially stable against attack by nucleases, the next challenge for a DNA vaccine delivery system is to efficiently cross the cell membrane carrying the p-DNA. The size of the particles of the present invention is well-suited for efficient cellular uptake by host cells after forming complexes with p-DNA, mRNA, siRNA or other nucleic acids. In some instances, where the nucleic acid molecules are located on the outside of the shell, secured to the particles via entanglement in the projections, it may not be necessary to use a shell with any porosity since the active molecules do not substantially enter the internal cavity.

Accordingly, in a sixth aspect, the present invention provides a composition comprising rough nanoparticles at least partially coated with one or more nucleic acids. The rough nanoparticles may have little or no porosity. The rough nanoparticles may have a solid core or they may have a hollow core. The rough nanoparticles may have a mesoporous structure but, due to the size of the one or more nucleic acids, there may be little or no penetration of the pores of the nanoparticle by the one or more nucleic acids.

In a seventh aspect, the present invention provides particulate material comprising rough nanoparticles comprising a core, the external surface of which has projections thereon, the projections having smaller sizes than the particle size, the rough nanoparticles having a particle size ranging from 100 nm to 3000 nm, a size of the projections ranging from 5 nm to 1000 nm.

In this aspect, the size of the projections may range from 100 nm to 500 nm. The projections may comprise nanospheres on the shell or outgrowths on the shell. The core may comprise silica, Ag, Au, calcium phosphate or titanium dioxide or carbon or a carbon-based material. The nanoparticles may have a core having a diameter of from 100 nm to 1000 nm. The core may be a solid core or a hollow core. The nanoparticles have little or no porosity.

In an eight aspect, the present invention provides a composition comprising rough nanoparticles as claimed in any one of claims 79 to 85 at least partially coated with nucleic acids. The nucleic acid may be selected from one or more of plasmid DNA (p-DNA) and messenger RNA (mRNA).

In a ninth aspect, the present invention provides use of rough mesoporous hollow nanoparticles in accordance with the seventh aspect of the present invention for vehicles for delivery of hydrophobic material to biological systems.

In a tenth aspect, the present invention provides use of rough mesoporous hollow nanoparticles in accordance with the seventh aspect of the present invention for drug delivery of hydrophobic drugs, or as carriers and delivery agents for hydrophobic proteins or as carriers and delivery agents for hydrophobic dyes that can be used as marker agents.

In an eleventh aspect, the present invention provides use of rough mesoporous hollow nanoparticles in accordance with the seventh aspect of the present invention for removal of water pollutants or in surface coatings for self-cleaning applications. The particles may be modified with hydrophobic compounds to yield superhydrophobic particles.

In a twelfth aspect, the present invention provides a method for forming rough nanoparticles comprising the steps of forming a particle from a reaction mixture, the particle being formed from a first material, adding a precursor of a second material to the reaction mixture to form a shell of the second material around the particle, the shell having outgrowths of the second material extending therefrom with first material being formed from the reaction mixture between the outgrowths of the second material and subsequently removing the first material located exteriorly to the shell. The shell may comprise a solid shell having little or no porosity. The step of removing the first material located exteriorly to the shell may leave a core of first material inside the shell.

In some embodiments, the nucleic acid may be plasmid DNA or mRNA. Two or more nucleic acids may be used.

Where the nucleic acid comprises plasmid DNA, the composition may comprise a DNA vaccine composition.

In one embodiment of the present invention, rough mesoporous hollow nanoparticles may be prepared by forming a hollow shell nanoparticle and adding nano particles with smaller sizes onto the hollow shell nanoparticles of relatively larger size so that the smaller particles form outgrowths or projections on the outer surface of the larger hollow shell. The hollow silica nanoparticles may be mesoporous. According to this approach, the particles that will form the projections may be synthesised separately to the larger hollow shells.

In one embodiment of the present invention, rough mesoporous hollow silica nanoparticles may be prepared by forming a hollow silica shell nanoparticle and adding silica nano particles with smaller sizes onto the hollow silica shell nanoparticles of relatively larger size so that the smaller silica particles form outgrowths or projections on the outer surface of the larger hollow silica shell. The hollow silica shell nanoparticles may be mesoporous. According to this approach, the silica particles that will form the projections may be synthesised separately to the larger hollow silica shells.

In another embodiment, the rough mesoporous hollow nanoparticles may be formed by forming a sacrificial particle from a reaction mixture, the sacrificial particle being formed from a carbon-based material, adding a shell material precursor to the reaction mixture to form a porous shell around the sacrificial particle, the shell having outgrowths of material containing silicon extending therefrom with carbon-based material being formed from the reaction mixture and being deposited between the outgrowths of material and subsequently removing the carbon-based material. Here, the outgrowth material or outgrowth material precursor and carbon-based material are co-deposited onto the porous shell in a spatially inhomogeneous manner such that subsequent removal of the carbon-based material leaves projections of material protruding from the surface of the shell. The carbon-based material co-deposited with the projections may be deposited from the carbon-based precursor left over from the formation of the sacrificial particles or carbon-based precursor may be subsequently added to the mixture. It is believed that this fabrication method is unique.

In another embodiment, the rough mesoporous hollow silica nanoparticles may be formed by forming a sacrificial particle from a reaction mixture, the sacrificial particle being formed from a carbon-based material, adding a silica precursor to the reaction mixture to form a porous shell containing silicon around the sacrificial particle, the shell containing silicon having outgrowths of material containing silicon extending therefrom with carbon-based material being formed from the reaction mixture between the outgrowths of material containing silicon and subsequently removing the carbon-based material. Here, silicon and carbon-based material are co-deposited onto the porous silicon shell in a spatially inhomogeneous manner such that subsequent removal of the carbon-based material leaves projections of silicon protruding from the surface of the silica shell. The carbon-based material co-deposited with the silicon projections may be deposited from the carbon-based precursor left over from the formation of the sacrificial particles or carbon-based precursor may be subsequently added to the mixture.

Accordingly, in a thirteenth aspect, the present invention provides a method for forming rough mesoporous hollow nanoparticles comprising the steps of forming a sacrificial particle from a reaction mixture, the sacrificial particle being formed from a first material, adding a precursor of a shell material to the reaction mixture to form a shell of a second material around the sacrificial particle, the shell having outgrowths of material extending therefrom with first material being formed from the reaction mixture between the outgrowths of the second material and subsequently removing the first material.

In one embodiment of this method, the first material is a carbon-based material and the second material is a silicon or silica-based material. In this embodiment, the method for forming rough mesoporous hollow nanoparticles comprising the steps of forming a sacrificial particle from a reaction mixture, the sacrificial particle being formed from a carbon-based material, adding a precursor of a shell material to the reaction mixture to form a shell around the sacrificial particle, the shell having outgrowths of material extending therefrom with carbon-based material being formed from the reaction mixture between the outgrowths of material and subsequently removing the carbon-based material. The sacrificial particle can be made from various polymerisation precursors, e.g. aminophenol-formaldehyde or dopamine.

In one embodiment, the carbon-based material comprises a polymer formed by the reaction of two or more monomers or polymer precursors. In one embodiment, the shell containing silicon and the outgrowths of material containing silicon comprise silica. In this embodiment, the silica precursor forms a silica shell around the sacrificial particle with outgrowths of silica extending therefrom.

In one embodiment, the silica precursor material forms silica at a faster rate than the formation of the carbon containing material. As a result, a shell of silica is first deposited on the surface of the preformed sacrificial particles. Typically, once the shell of silica has been formed, sufficient time has passed for the precursors to the carbon-based material to start forming additional carbon-based material. Therefore, the growth of carbon-based material competes with the growth of silica species on the shell of silica, which results in preferentially vertical outgrowths of the respective species. This results in the formation of a layer of "rod-like" silica projections and carbon-based material between the projections. When the silica species in the reaction mixture are consumed, the remaining precursors to the carbon-based material further deposit or react to form an outermost layer of carbon-based material. The carbon-based material may be removed by any suitable process, typically by heating, such as calcination, or by using an appropriate solvent. This method may also be used with particles made from materials other than silica, such as Ag, Au, calcium phosphate and titanium dioxide.

In instances where it is desired to form a nanoparticle having a solid core, the step of removing the first material may be controlled so that the core material is not removed. In instances where it is desired to form a particle having little or no porosity, the shell around the core is formed so that it is a shell having little or no porosity.

In one embodiment, the carbon-based material is formed from a reaction mixture that comprises resorcinol-formaldehyde, aminophenol-formaldehyde or dopamine. The sacrificial particles may be formed under typical Stöber synthesis conditions of ammonia aqueous solution, deionized water and ethanol with of pH=11.5 at room temperature. The weight ratio of silica precursor of TEOS to resorcinol and formaldehyde is typically 1:0.71 and 1:0.81, respectively. The silica precursor may comprise tetraethyl orthosilicate (TEOS), tetrapropyl orthosilicate (TPOS) or tetrabutoxysilane (TBOS), tetramethyl orthosilicate (TMOS) or other silica precursors known to those skilled in the art. Under the reaction conditions used, the silica precursor may form silica. Alternatively, the silica precursor may form a silicon containing material that may be subsequently converted to silica.

In one embodiment of the thirteenth aspect of the present invention, the silica precursor is added to the reaction mixture and a further addition of precursors for the carbon-based material is subsequently made at a later time.

In one embodiment, one or more of the precursors for the carbon-based material in the reaction mixture are essentially fully consumed in forming the sacrificial particle, following which the precursor for the shell material is added and further of the precursors for the carbon-based material are added a predetermined period after addition of the shell material precursor. This allows the shell to form around the sacrificial particle. This shell will surround the hollow core in the final rough mesoporous hollow nanoparticle. In another embodiment, the shell material precursor forms material at a significantly faster rate than the precursors for the carbon-based material. This will also result in the formation of a shell around the sacrificial particle. However, formation of the carbon-based material from its precursors will still occur and this will tend to occur on the surface of the shell or silicon containing shell in competition with the deposition of further shell material. As a result, separate islands of carbon-based material and shell material will form on the surface of the shell. Further deposition of the carbon-based material will tend to occur on the islands of carbon-based material, leading to outgrowths of carbon-based material. Similarly, further deposition of the shell material will tend to occur on the islands of shell material, leading to outgrowths of the shell material. Thus, rod-like outgrowths of each material will occur. Once the shell material precursor has been exhausted, further carbon-based material will be deposited to form an outer shell of carbon-based material. Removal of the carbon-based material, such as by calcination in air, results in the formation of the rough mesoporous hollow nanoparticles.

In one embodiment in which the rough mesoporous hollow nanoparticles comprise rough mesoporous hollow silica nanoparticles one or more of the precursors for the carbon-based material in the reaction mixture are essentially fully consumed in forming the sacrificial particle, following which the silica precursor is added and further of the precursors for the carbon-based material are added a predetermined period after addition of the silica precursor. This allows the silica or silicon containing shell to form around the sacrificial particle. This silica or silicon containing shell will surround the hollow core in the final rough mesoporous hollow silica nanoparticle. In another embodiment, the silica precursor forms silica or silicon containing material at a significantly faster rate than the precursors for the carbon-based material. This will also result in the formation of a silica shell or silicon containing shell around the sacrificial particle. However, formation of the carbon-based material from its precursors will still occur and this will tend to occur on the surface of the silica shell or silicon containing shell in competition with the deposition of further silica or silicon containing material. As a result, separate islands of carbon-based material and silica/silicon containing material will form on the surface of the silica/silicon containing material shell. Further deposition of the carbon-based material will tend to occur on the islands of carbon-based material, leading to outgrowths of carbon-based material. Similarly, further deposition of the silica/silicon containing material will tend to occur on the islands of silica/silicon containing material, leading to outgrowths of silica/silicon containing material. Thus, rod-like outgrowths of each material will occur. Once the silica precursor has been exhausted, further carbon-based material will be deposited to form an outer shell of carbon-based material. Removal of the carbon-based material, such as by calcination in air, results in the formation of the rough mesoporous hollow silica nanoparticles.

The amount of shell material precursor that is added to the reaction mixture may be controlled to control the thickness of the shell, the porosity of the shell and the spacing between the outgrowths. In some embodiments, the shell that is formed on the surface of the sacrificial particle may comprise a discontinuous shell having gaps or spaces therein. Indeed, in some embodiments, the shell may comprise a discontinuous material layer or a relatively continuous interlinked material layer.

The reaction conditions and reaction time may be controlled in order to control the size of the sacrificial particle that is first formed. This will, of course, allow for control of the size of the hollow core of the final rough mesoporous hollow nanoparticles. It will be appreciated that the shell that defines the hollow core of the final rough mesoporous hollow nanoparticles may shrink during the step of removing the carbon-based material.

In a fourteenth aspect, the present invention provides a method for forming carbon nanoparticles comprising the steps of forming a reaction mixture containing a silica precursor and one or more precursors of carbon-based material wherein silica or silicon containing particles are formed and carbon-based materials form on the silica or silicon containing particles to thereby form a shell of carbon-based material on the silica or silicon containing particles, adding further silica precursor to the reaction mixture to form further silica or silicon containing material on the shell of carbon-based material, wherein further carbon-based material is formed and deposits between and over the further silica or silicon containing material, and removing the silica or silicon containing material to thereby obtain carbon nanoparticles. The silica or silicon containing material could be replaced by other materials, e.g. titanium dioxide derived from aluminium isopropoxide or aluminium oxide from titanium (IV) butoxide. The obtained nanoparticles can be N-doped compositions of carbon nanoparticles by replacing RF with aminophenol-formaldehyde or dopamine containing N as polymerisation precursors in alcohol-water system.

In a fifteenth aspect, the present invention provides a method for forming carbon nanoparticles comprising the steps of forming a reaction mixture containing a precursor of a first material and one or more precursors of carbon-based material wherein particles of the first material are formed and carbon-based materials form on the particles of first material to thereby form a shell of carbon-based material on the particles of first material, adding further first material precursor to the reaction mixture to form further first material on the shell of carbon-based material, wherein further carbon-based material is formed and deposits between and over the further first material, and removing the first material to thereby obtain carbon nanoparticles.

In one embodiment, the carbon-based material is carbonised. The carbon-based material may be carbonised before removal of the first material. In one embodiment, the particle is subjected to a hydrothermal treatment prior to the carbonisation step.

The carbon nano particles formed in the method of the eighth and ninth aspects of the invention comprise mesostructured hollow carbon spheres having a bilayered structure. By controlling the thickness of the carbon/silica or carbon/first material shells, the bilayered morphology of the particles and the mesopore size can be regulated. The bilayered morphology may comprise invaginated, endo-invaginated or intact spheres. The diameter of the carbon nanoparticle and hollow core size may be controlled to range from 100-1000 nm, the thickness of the wall surrounding the hollow core can be adjusted from 5-100 nm. The pore volume and surface area of the bilayered carbon nanoparticles may be in the range of 1-3 $cm^3$ $g^{-1}$ and 800-1300 $m^2$ $g^{-1}$, respectively.

In a sixteenth aspect, the present invention provides carbon particles comprising comprise mesostructured hollow carbon spheres having a bilayered structure. The bilayered morphology may comprise invaginated, endo-invaginated or intact spheres. The diameter of the carbon nanoparticle and hollow core size may range from 100-1000 nm, the thickness of the wall surrounding the hollow core may range from 5-100 nm. The pore volume and surface area of the bilayered carbon nanoparticles may be in the range of 1-3 $cm^3$ $g^{-1}$ and 800-1300 $m^2$ $g^{-1}$, respectively. The bilayered structure may comprise two spaced partial or complete carbon shells, with the inner shell being essentially hollow. The carbon particles may have a multi-layered structure, having 2 or more spaced partial or complete carbon shells.

In the field of energy storage, the desire to achieve higher energy densities is driving investigation of new high capacity electrode materials. However, unlike established materials such as graphite as used in lithium ion batteries, some of these promising high capacity candidate materials suffer from poor electronic conductivity and in some cases their cycling involves significant volume changes. These limitations can result in poor power capability and cycle life respectively. The inventors of the present invention have found that the carbon nanoparticles of the present invention can be used as a carrier or encapsulant for electrode materials that suffer from these challenges. Battery active materials may be loaded into the carbon particles which are inherently good conductors of electrons such that the active material is located within the internal cavity, in between the carbon walls, on the outside of the particles or any combination of these locations. By being in very close contact with the carbon particle, electronic conductivity challenges of the active material are minimised. In addition, the encapsulation of the active material confines it and restricts movement and subsequent loss of active material from the electrode as a result of volume changes during cycling, resulting in improved cycle life for the battery. The composition of battery active materials that may be used in the present invention include those materials that suffer from poor electronic conductivity and poor cycle life. These materials are well known to those skilled in the art and include sulfur and sulfur derivatives such as selenium sulfide ($SeS_2$). Other electrode active materials may include sulphur and sulphur containing compounds, silicon and mixtures containing silicon, tin and tin-containing alloys and mixtures, antimony and antimony-containing alloys and mixtures or any combination of these. Indeed, the present invention emcompasses any material known to be suitable for use as such by the person skilled in the art.

Accordingly, in a further aspect, the present invention provides a material for use in a battery or other electric power storage device comprising carbon particles as described above loaded with one or more electrode active materials.

By "electrode active electric materials" we mean a material that can accept electric charge to reach a charged state and subsequently discharge electricity to move toward a discharged state.

In embodiments of this aspect of the present invention, the material may be used as a battery electrode material, in a battery electrode, or in a battery cell, or in a capacitor, supercapacitor or a pseudo capacitor, or in an electrochromic device, or indeed in any application where use of a material that can be charged and discharged is required.

In one embodiment of the seventh, eighth or ninth aspects of the invention, the silica precursor comprises tetraethyl orthosilicate (TEOS). The precursors for the carbon-based material may comprise resorcinol and formaldehyde.

In one embodiment, the silica or silicon containing material is removed by etching or by dissolution. For example, the silica or silicon containing material may be removed by etching or dissolving in HF (5%) aqueous solution or sodium hydroxide (1M) solution.

In one embodiment, the invention provides a composition comprising an insecticidal composition for external application to an animal or plant, the composition comprising rough mesoporous hollow nanoparticles having one or more hydrophobic insecticidal materials therein or thereon, the rough mesoporous hollow nanoparticles comprise rough mesoporous hollow silica nanoparticles, the one or more hydrophobic materials being present in the hollow core of the nanoparticles and/or in the spaces between raised or projecting regions that produce the surface roughness of the nanoparticles.

Any of the features described herein can be combined in any combination with any one or more of the other features described herein within the scope of the invention.

BRIEF DESCRIPTION OF DRAWINGS

Various embodiments of the invention will be described with reference to the following drawings, in which.

DESCRIPTION OF EMBODIMENTS

Figure 1:
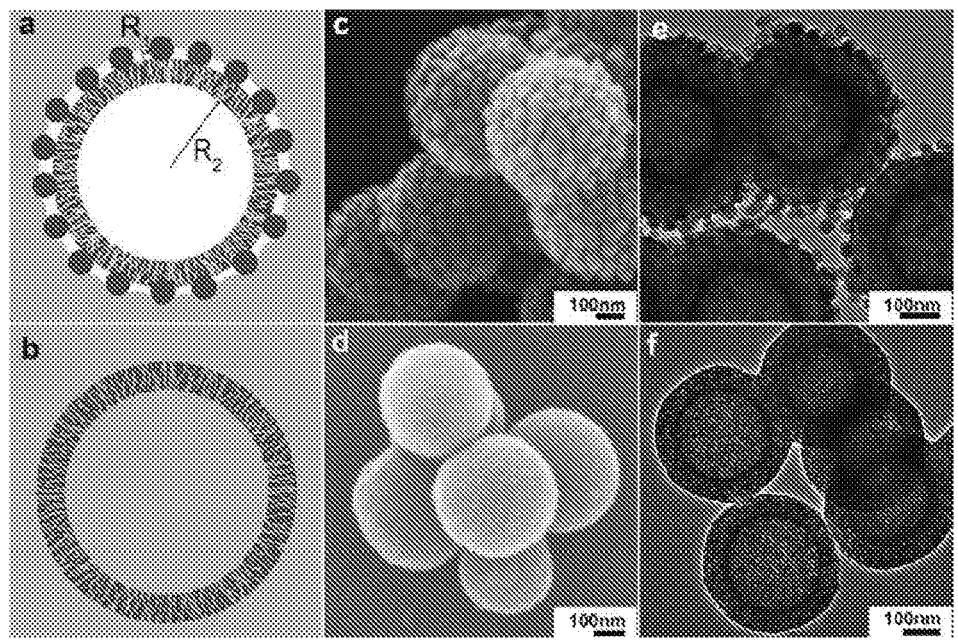
FIG. 1 shows a schematic diagrams of (a) MSHSs-RS and (b) MSHSs-SS, where (b) shows the porous shell surrounding the inner cavity, R2 represents the radius of the cavity, R1 represents the radius of spherical projections on the surface of the shell and white areas between the spherical projections show the presence of air when particles are immersed in water, providing some hydrophobic character to the particles. SEM (c and d), TEM images (e and f) of MSHSs-RS and MSHSs-SS.

Throughout the examples, the following abbreviations will be used:

MSHS—mesoporous silica hollow spheres (having a relatively smooth surface).

MSHS-RS—mesoporous silica hollow spheres with a rough surface.

Example 1

Development of a Nano-Pesticide with Improved Safety and Performance.

Ticks and buffalo fly cause over $400 million/year in economic losses to the Australian livestock industry and are currently treated with highly toxic synthetic pesticides. Spinosad, a naturally derived pesticide with low environmental impact and low toxicity will be loaded into silica hollow spheres which will improve adhesion to skin/hair and protect against UV degradation. The nano-spinosad pesticide will have enhanced efficacy and effective duration in field conditions compared to conventional pesticides, significantly reducing the cost of pest control.

Spinosad was supplied by the Elanco Animal Health. Mesoporous silica hollow spheres with a rough surface (MSHSs-RS) and a smooth surface (MSHSs-SS) were synthesized in Yu Group in Australian Institute for Bioengineering and Nanotechnology, University of Queensland. Kangaroo skin samples with fur were purchased from Skinny Shop, Australia as an animal model. The skin samples were washed thoroughly by distilled water and cut into small pieces at 1 $cm^2$ before the tests. All the other reagents were of analytical reagent grade.

Adhesive Property of Nanoparticles on Animal Skin Fur

The adhesive behaviour of the nanoparticles on animal fur was evaluated on a treated kangaroo skin with fur as an animal model. Silica nanoparticles (2 mg/$cm^2$) were dispersed in an ethanol solution and the solution was dripped homogenously on the fur side of the kangaroo skin pieces (1 $cm^2$). Skin pieces were then allowed to dry at 40° C. overnight. The attachment of the nanoparticles on hair was observed by confocal microscopy (LSM ZEISS 710) before and after several washings with water. Pure skin samples and silica nanoparticles (using MSHSs-RS as an example) were also observed under the microscope. Quantitative amount of the attached nanoparticles before and after washing were measured and compared by inductively coupled plasma optical emission spectrometry (ICPOES, a Vista-PRO instrument, Varian Inc, Australia). Skin samples containing the nanoparticles were dissolved in 2M NaOH overnight under stirring to allow dissolution of the silica nanoparticles and silicon concentration were measured. Silicon amount of similar size skin without nanoparticles were also measured as the blank.

Preparation of Nano-Spinosad

A rotary evaporation method was utilized for encapsulation of spinosad into the silica nanoparticles. In the procedure, 34 mg of silica nanoparticles after calcination were added to 8, 10 or 12 ml spinosad in ethanal solution (1.7 mg/ml), with a spinosad:silica feeding ratio of 0.4:1, 0.5:1 and 0.6:1, respectively (hereinafter denoted as nano-spinosad-X, where X is the ratio of spinosad:silica). The mixture was removed into a long cylindrical flask attached to a rotary evaporator (BUCHI R-210) and evaporated at 40° C. in a vacuum system in dark with a residual pressure of 175 mbar until all solvent had been removed. For comparison purposes, a similar procedure was been carried out with spinosad-ethanol solution only (no nano-particles being present).

Characterization

The morphologies of the silica nanoparticles before and after the loading of spinosad were observed using and JEOL JSM 7800 field emission scanning electron microscope (FE-SEM) operated at 0.8-1.5 kV. For FE-SEM measurements of pure silica nanoparticles, the samples were prepared by dispersing the powder samples in ethanol, after which they were dropped to the aluminium foil pieces and attached to conductive carbon film on SEM mounts. For FE-SEM measurements of nano-spinosad, the samples were directly attached to the conductive carbon film on SEM mounts. Transmission electron microscopy (TEM) images of the silica nanopartices were obtained with JEOL 2100 operated at 200 kV. For TEM measurements, the samples were prepared by dispersing and drying the powder samples-ethanol dispersion on carbon film on a Cu grid. Fourier transform infrared (FTIR) spectra were collected on a ThermoNicolet Nexus 6700 FTIR spectrometer equipped with a Diamond ATR (attenuated total reflection) Crystal. For each spectrum, 32 scans were collected at resolution of 4 cm-1 over the range 400-4000 cm-1. Wide angle X-ray diffraction (WA-XRD) patterns of the materials were recorded on a German Bruker D8 X-ray diffractometer with Ni-filtered Cu Kα Radiation. A Metter Toledo GC200 thermogravimetric analysis (TGA) station was used for the loading amount and differential scanning calorimetry (DSC) study at a heating rate of 2° C. min-1.

Release Test of Nano-Spinosad

In a release test, 2.67 mg nano-spinosad-X (containing 1 mg spinosad) was dispersed in 1 ml distilled water, respectively. The mixtures were kept at 25° C. incubator at 200 rpm. The supernatants were collected at different time and the released amount of spinosad was measured and evaluated by using a UV-Vis spectrophotometer at a wavelength of 248 nm. The release amount of pure spinosad in water was also tested using the same procedure.

UV-Stability Test of Nano-Spinosad

In this test, 1.2 mg pure spinosad and 4.2 mg nano-spinosad-0.4 (containing 1.2 mg spinosad) were added in two transparent quartz containers, respectively. The using of quartz containers is to minimized the shielding of UV light from the containers. Each of the sample was placed under the UV light with a wavelength of 365 nm and power of 17.77 mV $cm^{-3}$. All samples were irradiated by the UV light for 2 hours. After the irradiation, the spinosad and its degradation products were extracted by acetonitrile (ACN) for three times and the final concentration was diluted to. 0.5 mg/ml dispersed in 1 ml distilled water. The UV degradation conditions of both pure spinosad and nano-spinosad-0.4 were tested by high-performance liquid chromatography (HPLC) using ACN as the mobile phase.

In Vitro Bio-Assay

The in vitro effects of spinosad and nano-spinosad on the cattle tick, *Rhipicephalus microplus* were evaluated. The test was conducted at Biosecurity Sciences Laboratory (Queensland Government) using a standard Larval Immersion Test using organic solvent to extract the actives.

Preparation of MSHSs-RS

As shown in FIG. 1a MSHSs-RS particles were prepared by adding silica shell particles with smaller sizes (~30 nm in diameter) onto MSHSs with relatively larger sizes (~400 nm). On the surface of MSHSs-RS particles, a void space between the small shell spheres with a radius of R1 (FIG. 1a) is generated for air entrapment. The air pocket is significantly enlarged in these MSHS-RS particles because the internal spherical cavity with a radius of R2 (R2>>R1) is connected with the air through the mesopores in the silica shell. The repulsion of the trapped air in the void spaces towards water molecules provides the energy barrier against the wetting process because the hydroxyl groups in silica tend to absorb water molecules, as in the case of MSHSs (as shown in FIG. 1b). Therefore, the designed MSHSs-RS should demonstrate increased hydrophobicity compared to MSHSs although both materials have the same pure silica composition. It is also advantageous compared to a solid nanoparticle with a rough surface because the solid nanoparticle with a rough surface has less air pockets (no hollow core having a radius of R2) and limited loading capacity of hydrophobic drugs. Previous studies mainly focused on large flat surfaces; nanoparticles with hydrophilic compositions and hydrophobic properties through surface roughness control have not been reported and have not been demonstrated for bio-applications. Images of the prepared MSHSs-RS were taken using a scanning electron microscope (SEM) and a transmission electron microscope (TEM) (see FIGS. 1c, 1e). For comparison MSHSs with a smooth surface were also prepared and characterised as shown in FIGS. 1d and 1f. Both nanoparticles have uniform and hollow spherical morphology with the surface of MSHS-RS homogeneously decorated with silica shell particles. In accordance with our theory, MSHSs-RS nanoparticles show unusual hydrophobic properties. Hydrophobicity was directly observed by the dispersion of nanoparticles in a mixed solvent of water/diethyl ether. MSHSs-RS preferentially rests at the bottom of the diethyl ether layer (a hydrophobic solvent) while MSHSs directly disperses in the water layer. TGA profiles presented a small weight loss of 0.9% below 200° C. for MSHSs-RS and 7.2% for MSHSs which can be attributed to the evaporation of moisture, indicating that the introduction of surface roughness makes MSHSs-RS more hydrophobic and thus it absorbs less moisture from the atmosphere than MSHSs.

To provide a quantitative comparison of the hydrophobicity between MSHSs-RS and MSHSs, a gel trapping technique (GTT) was employed and revealed that MSHSs-RS have a contact angle value of 107.5°±10 whilst that of MSHSs was 72.5°±5. The contact angle value of MSHSs-RS is slightly lower than that obtained for the octadecyltrimethoxysilane modified silica (~136°). Compared to MSHSs, MSHSs-RS exhibits consistently higher loading capacity for a range of hydrophobic molecules, including RNase A (RNASE), insulin (INS), lysozyme (LYS), a hydrophobic dye, disperse red 1 (DR1) and a hydrophobic drug, griseofulvin (GRIS). These results further confirm that enhanced surface hydrophobicity of MSHS-RS nanoparticles increases the loading capacity of hydrophobic molecules.

Figure 2:
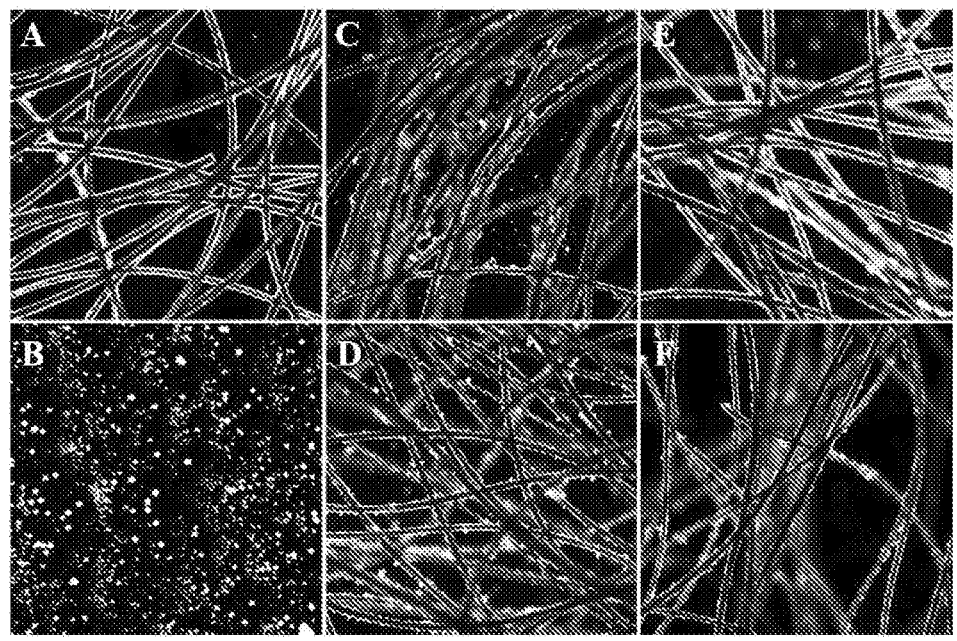
FIG. 2 shows optical images (phase contrast) of (A) kangaroo fur, (B) silica nanoparticles MSHSs-RS, kangaroo fur treated with (C, E) MSHSs-SS and (D, F) MSHSs-RS (E and F are samples washed by water)

To test the adhesion of MSHSs-RS, animal fur was used as a model. MSHSs-RS and MSHSs with the same weight were dispersed in water and homogeneously applied to two pieces of fur with the same size. After drying and washing with water three times, the silica content remaining on fur was measured. FIG. 2A is the optical image of kangaroo fur that illustrates typical hair structure. In comparison, pure silica shows white particles under optical microscope due to its powder nature (FIG. 2B). After application of silica nanoparticles onto the fur samples, white particles were observed attaching on the surface of the hairs, indicating the attachment of both silica nanoparticles (FIGS. 2C and 2D). After three times washing, there are more white particles attached onto the kangaroo hairs than in the case of MSHSs-RS (FIG. 2E) compared to that of MSHSs-SS (FIG. 2F). This phenomenon indicates that MSHSs-RS have stronger adhesion ability on animal hairs. This conclusion is also supported from the ICPOES results. The silica weight percentage remaining on fur for MSHSs and MSHSs-RS was 28.5% and 51.0%, respectively. MSHSs-RS shows significantly improved adhesion due to its rough surface and hydrophobicity. The enhanced adhesion of MSHSs-RS nanoparticles on fur should prolong the effective duration of Spinosad-MSHSs-RS nano-formulation in field conditions.

Figure 3:
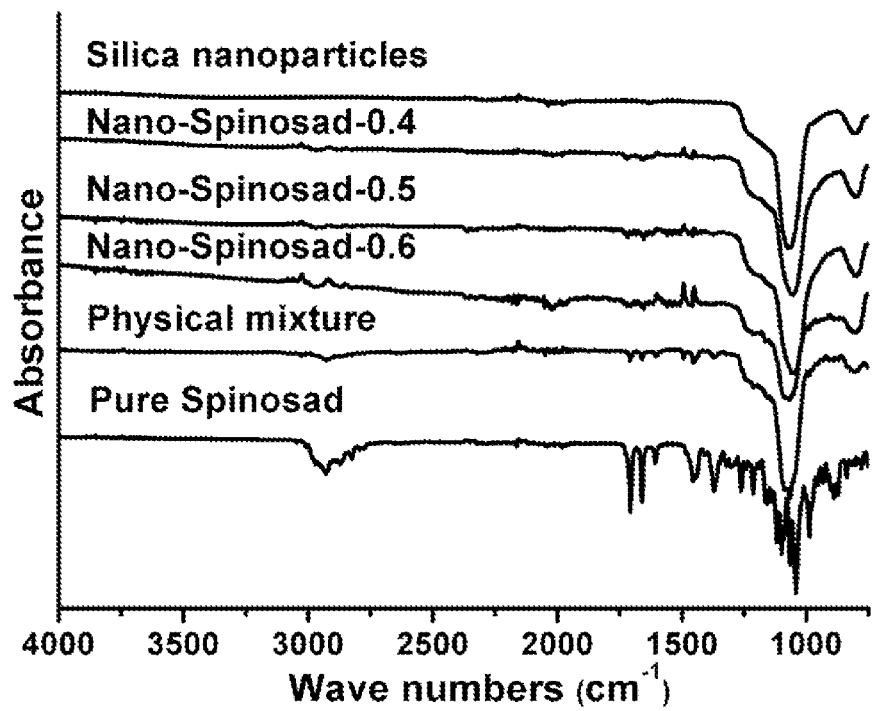
FIG. 3 shows FTIR spectra of a series of samples including pure spinosad, nano-spinosad-X, silica nanoparticles and the physical mixture of spinosad and silica nanoparticles.

A rotary evaporation method was utilized to encapsulate spinosad into silica nanoparticles using spinosad-ethanol solution with spinosad:silica ratio of 0.4:1, 0.5:1 and 0.6:1. The nano-spinosad composites are denoted nano-spinosad-X where X stands for the ratio of spinosad and silica. FIG. 3 shows the FTIR spectrum of pure spinosad with obvious characteristic peaks at 891, 987, 1041, 1099, 1213, 1263, 1371, 1456, 1660, 1707 and in the range of 2787-3012 cm$^{-1}$. The spectrum of silica nanoparticles shows a characteristic peak at 810 cm$^{-1}$ that can be attributed to v(Si—O), and broad peak in the range of 1050-1200 cm$^{-1}$ that can be attributed to —Si—O—Si bonding. In the spectra of all nano-spinsad-X, characteristic peaks 1371, 1456, 1660, 1707 and in the range of 2787-3012 cm$^{-1}$ can still be observed besides overlapping with the characteristic peaks of silica. The FTIR spectra confirm the successful encapsulation of spinosad with silica nanoparticles.

Figures 4A, 4B:
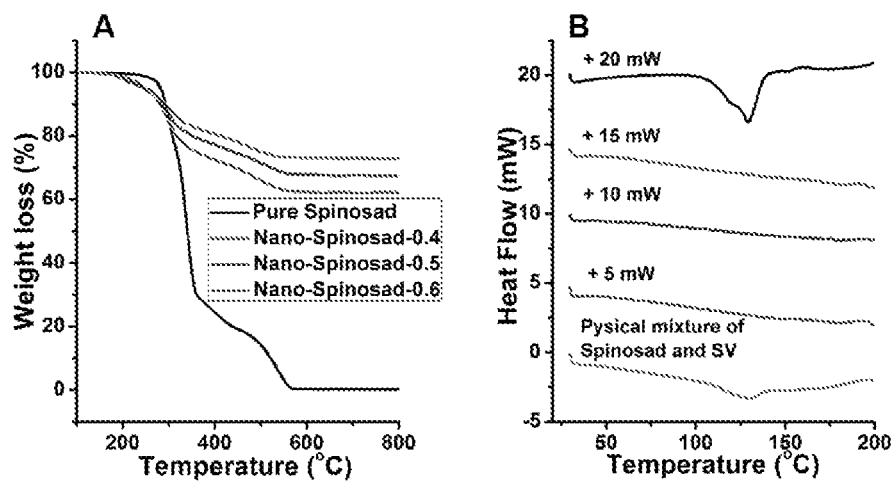
FIG. 4 shows (A) TGA profiles and (B) DSC profiles of (black) pure spinosad, (red) nano-spinosad-0.4, (blue) nano-spinosad-0.5, (d) nano-spinosad-0.6. (pink in B is the DSC curve for physical mixture of spinosad and silica nanoparticles)

The actual loading amount of spinosad can be calculated by the weight loss from TGA results (FIG. 4A). Pure spinosad shows complete weight loss of 99.9% at 900° C. Pure silica nanoparticles after calcination shows negligible weight loss from the adsorbed moisture (data no shown). The weight losses of nano-spinosad-X are 27.4, 32.8 and 38.1% for X=0.4, 0.5 and 0.6, respectively. Accordingly, the loading amount of nano-spinosad-X (X=0.4, 0.5 and 0.6) is calculated to be 28.6, 33.3 and 37.5%, respectively, indicating that rotary evaporation can achieve complete loading (~100%) of spinosad.

Figure 5:
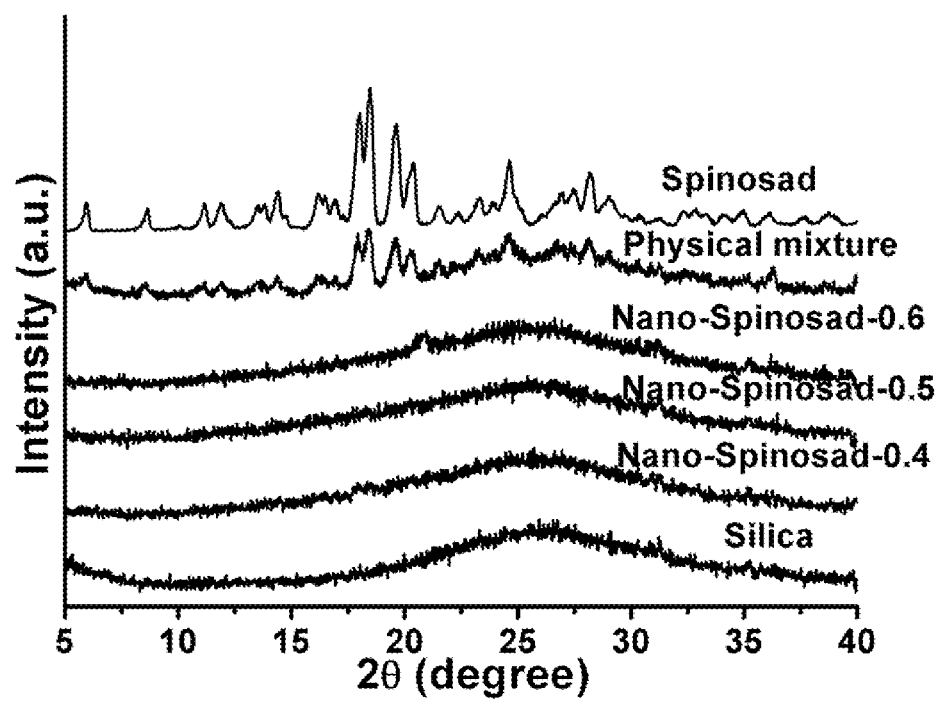
FIG. 5 shows wide angle XRD patterns of a series of samples including pure spinosad, nano-spinosad-X, silica nanoparticles and the physical mixture of spinosad and silica nanoparticles.

The crystalline state of spinosad before and after encapsulation is characterized by WA-XRD (FIG. 5). The WA-XRD pattern of pure spinosad shows a series of sharp peaks in the range of 5-40°, indicating pure spinosad is in a crystalline state. Pure silica nanoparticles show a broad peak centred at ~22° which can be attributed to amorphous silica. Sharp characteristic peaks could not be observed in the WA-XRD pattern of all samples of nano-spinosad-X beside the broad peak at 22° of amorphous silica, indicating no crystalline spinosad is formed in these samples. The crystallization behaviour of nano-spinosad-X has also been studied by DSC (FIG. 4B). Pure spinosad displays a sharp endothermic peak at 129° C. which indicates the melting point of crystalline spinosad. Similar to pure silica, all nano-spinosad-X show no obvious peaks in the range of 25-350° C., indicating an amorphous state. In comparison, a small endothermic peak at 129° C. is observed for the physical mixture of spinosad and silica (pink), indicating the existence of crystalline spinosad structure. The above results indicate that spinosad was encapsulated into MSHS-RS nanoparticles in a nano-dispersed form by utilizing the rotary evaporation technique.

Figure 6:
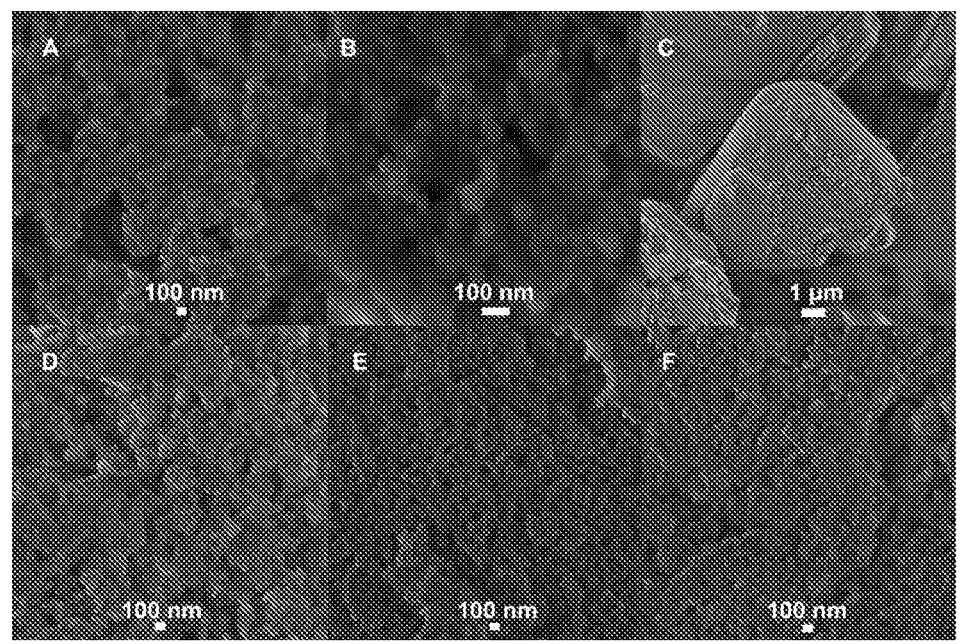
FIG. 6 shows FE-SEM images of pure silica nanoparticles in (A) low and (B) high magnifications, (C) pure spinosad, (D) nano-spinosad-0.4, (E) nano-spinosad-0.5 and (F) nano-spinosad-0.6.

FE-SEM was used to directly observe the morphology of nano-spinosad (FIG. 6). The FE-SEM images show that silica nanoparticles are aggregated in low magnifications (FIG. 6A) and spherical morphology in high magnifications (FIG. 6B). If pure spinosad-ethanol solution is used for rotary evaporation, large crystalline spinosad with the size of ~20 μm (FIG. 6C) is formed. In the same magnification, all nano-spinosad-X show aggregations of small particles (FIG. 6D-FIG. 6F) which are exactly the same morphology as pure silica without obvious crystals. These phenomena indicate the spinosad is successfully encapsulated in the cavity of MSHS-RS nanoparticles in different feeding ratios.

Figure 7:
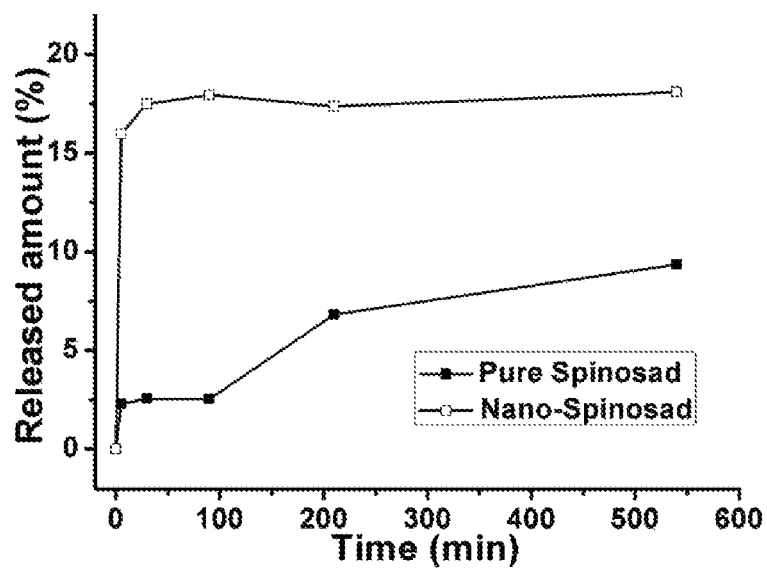
FIG. 7 shows time dependent release profiles of pure spinosad and nano-spinosad.

The release profile of both pure spinosad and nano-spinosad were tested in water. As shown in FIG. 7, for nano-spinosad, 16% of spinosad was released in a short period time of 5 min and this level was maintained until 540 min (release in water monitored by UV-Vis at 248 nm). On the other hand, for pure spinosad, only 2.4% of spinosad was released at 5 min while the cumulative release is less than 8% even at 540 min. Spinosad confined in silica nanoparticles shows a solubility of ~0.2 mg/ml, which is more than two times higher than that of pure spinosad, similar to the solubility enhancement of curcumin confined inside mesoporous materials. Consequently, the release behaviour of spinosad is improved compared to the pure spinosad. The fast release of a higher concentration of spinosad is expected to be beneficial for the development of an "effective-immediately" nano-spinosad formulation.

Figure 8:
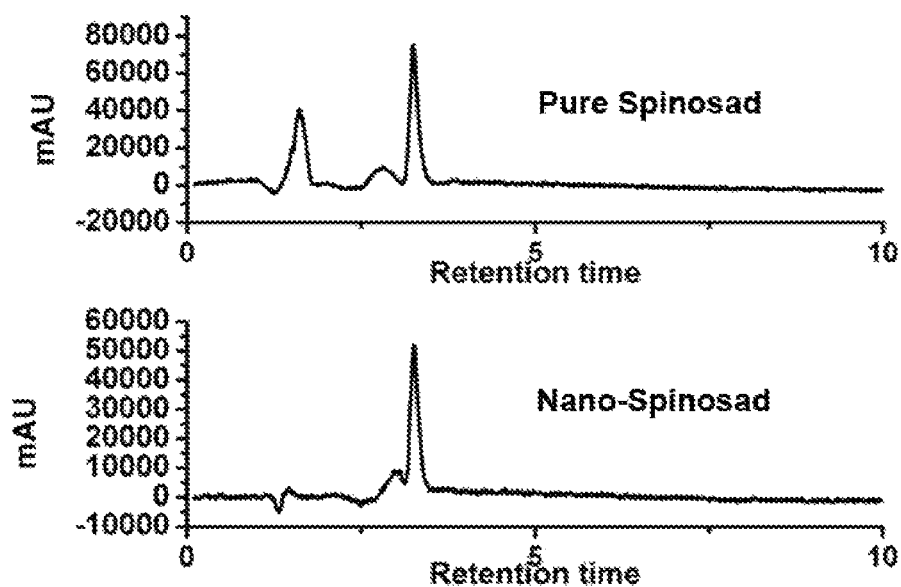
FIG. 8 shows HPLC patterns of pure spinosad and nano-spinosad after UV irradiation.

The UV stability of nano-spinosad was studied. Both spinosad and nano-spinosad were irradiated under UV light (wavelength 365 nm, 17.77 mV/cm$^3$) for 2 h followed by HPLC which was used to monitor the product after UV treatment utilizing ACN as the extraction media and mobile phase. As shown in FIG. 8, the peak at retention time of 3.5 min is attributed to spinosad. An additional peak at retention time of 1.5 min was also observed in the pure spinosad group, which can be attributed to the degraded product. This observation is in accordance with literature reports, indicating spinosad itself is UV labile. However, in the nano-spinosad group, the degradation peak is not observed, suggesting that the silica shell has a protective effect against UV irradiation for spinosad loaded inside the nano-cavity.

In order to confirm that the spinosad loaded into silica nanoparticles is still effective, we evaluated the in vitro effects of spinosad and nano-spinosad on the cattle tick, *Rhipicephalus microplus*. The test was conducted at Biosecurity Sciences Laboratory (Queensland Government) using a standard Larval Immersion Test. In the Larval Immersion Test, both spinosad and nano-Spinsad were firstly dissolved in organic solvent (2% Triton X-100 in acetone) to extract the actives for stock solution (10 mg/ml) and then be diluted in water. Both spinosad and nano-spinosad show dose-dependent mortality to cattle tick larval. Three assays were conducted to narrow the LC ranges. In Assay 3, the spinosad shows LC50 and LC99 value to larval cattle ticks of 54 and 196 ppm in 24 h, respectively. Nano-spinosad shows LC50 and LC99 value to larval cattle ticks of 46 and 159 ppm in 24 h, respectively. These results indicate of nano-spinosad show comparable and slightly better toxicity to tick larval models. This result confirms that after encapsulation the spinosad loaded in silica nanoparticles is still effective.

This example shows that MSHSs-RS show prolonged adhesion behaviour to animal fur. Using a rotary evaporation method, spinosad can be loaded into such hollow MSHS-RS nanoparticles with ~100% loading. The loading amount can reach up to 28.6-37.5% (wt/wt) as determined by TGA analysis, while WA-XRD and DSC analysis confirmed that spinosad was dispersed in the nano-cavity of the MSHS-RS in an amorphous state. Consequently, the release behaviour of spinosad is improved compared to the pure spinosad. Furthermore, the silica shell has a protective effect against UV irradiation for spinosad loaded inside the nano-cavity thus providing UV-shielding and protection of the labile spinosad. The nano-spinsad after loading in the cavity of the MSHS-RS is proved to be comparably effective to cattle tick larval (*Rhipicephalus microplus*). With enhanced water solubility, UV stability and fur adhesion of Spinosad-MSHSs-RS, this nanoformulation is expected to have prolonged duration of efficacy under field conditions.

Example 2—Forming MSHS-RS

This example describes an embodiment of the method of the third aspect of the invention for forming MSHS-RS nanoparticles.

Figure 9:
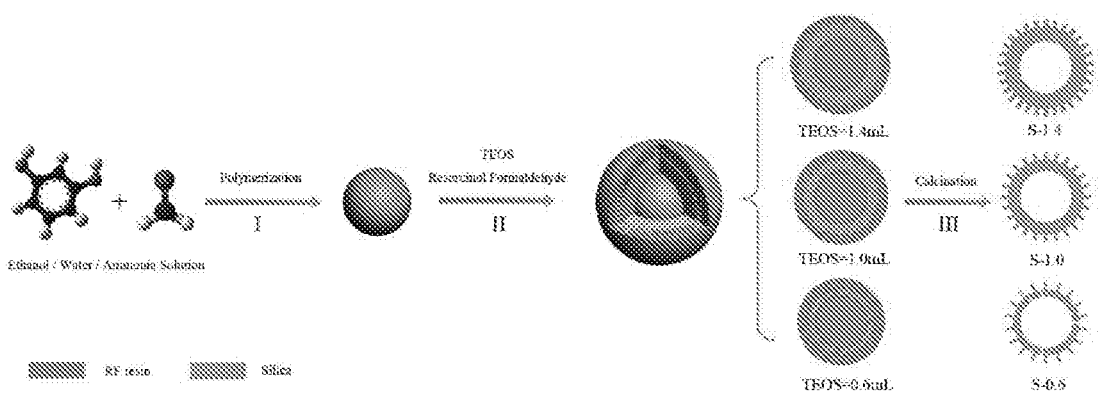
FIG. 9 shows a schematic illustration of the synthesis procedures of monodispersed rough silica hollow spheres in accordance with an embodiment of the third aspect of the present invention, as described in example 2.

The procedures for controlled synthesis of monodispersed rough silica hollow spheres are schematically illustrated in FIG. 9. In a typical Stöber synthesis condition, resorcinol (0.15 g) and formaldehyde (0.21 mL) were added into a basic solution with 70 mL of ethanol, 10 mL of water and 3 mL of ammonia (28 wt %) with a pH about 11.5 to form resorcinol-formaldehyde (RF) nanospheres at room temperature with a diameter of 180 nm after 6 h of polymerization. These RF nanospheres will form a sacrificial particle that will be eventually removed. Then, a certain amount of tetraethyl orthosilicate (TEOS) was added into the reaction solution, followed by another addition of resorcinol and formaldehyde 5 minutes later in Step II. Due to the difference between silica and RF deposition rates in Step II, a triple-layered shell was formed on the preformed RF core spheres. Specifically, a relatively dense silica layer was firstly deposited on the surface of preformed RF spheres, because of the faster condensation speed of silica oligomers compared with RF oligomers. Following passage of a certain time, when the RF oligomers started to polymerize, the intergrowth of RF along with the silica species started on the surface of the first silica layer, followed by a preferentially vertical growth of these two species. This resulted in the formation of hybrid second layer of 'rod-like' silica and RF. With the consumption of silica species, the remaining RF oligomers further deposited on the second layer to form an outmost layer of pure RF. By adjusting the amount of TEOS from 1.4 to 0.6 mL added in Step II, the thickness of the first silica layer reduced and the distance between the 'rod-like' silica enlarged due to the decreasing condensation rate of silica species. It should be noted that, with only 0.6 mL of TEOS added, the first silica layer is not continuous with some crevices existed. This may result from the discrete distribution of silica nuclei on the pre-formed RF surface and slow growth before merging together to form a relatively continuous interlinked silica layer. After calcination in air in Step III, the RF species in the hybrid composites were removed, leaving the silica hollow spheres with rough surface. The final silica products are denoted as S-1.4, S-1.0 and S-0.6 where the number represents the volume amount of TEOS addition in Step II.

The representative transmission electron microscopy (TEM) images of S-1.4, S-1.0 and S-0.6 are shown in FIGS. 10A-10C. Monodispersed silica hollow sphere with rough surface were observed in all the samples. The average particle size of S-1.4, S-1.0 and S-0.6 is estimated to be 300, 280 and 250 nm, respectively. The hollow cavity size of three samples is almost the same at about 160 nm, which is relatively smaller than the size of preformed RF nanospheres (180 nm). This may be caused by shrinkage during calcination. The 'rod-like' rough structure on the shell can be clearly identified from the TEM images, and a decreasing density of silica 'rod' distribution on the shell can also be revealed. Dynamic light scattering (DLS) analysis was further utilized to determine the particle size and monodispersity. As shown in FIG. 10D, the hydrodynamic diameter of S-1.4, S-1.0 and S-0.6 is about 295, 310 and 325 nm, respectively, which is slightly larger than those determined by TEM due to surrounded water molecules. The narrow particle size distribution curves with a small polydispersity index (PDI) value (0.053, 0.086, and 0.101 for S-1.4, S-1.0 and S-0.6 respectively) indicate all of the silica hollow spheres possess uniform particle sizes and excellent monodispersity.

Figure 10:
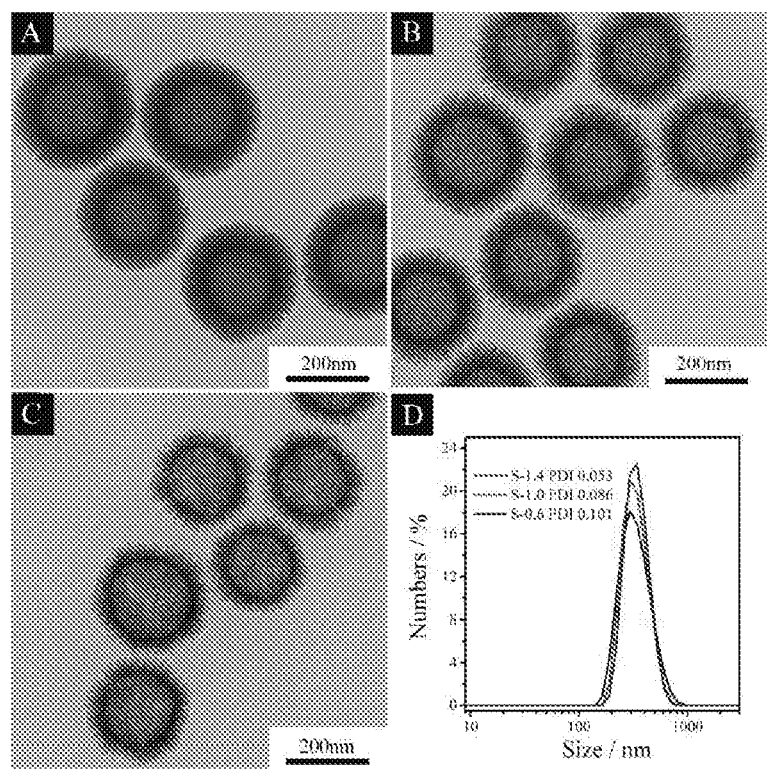
FIG. 10 shows TEM images (A, B, C) and DLS measurement (D) of rough surface silica hollow spheres S-1.4, S-1.0 and S-1.2 made in example 2.
Figure 11:
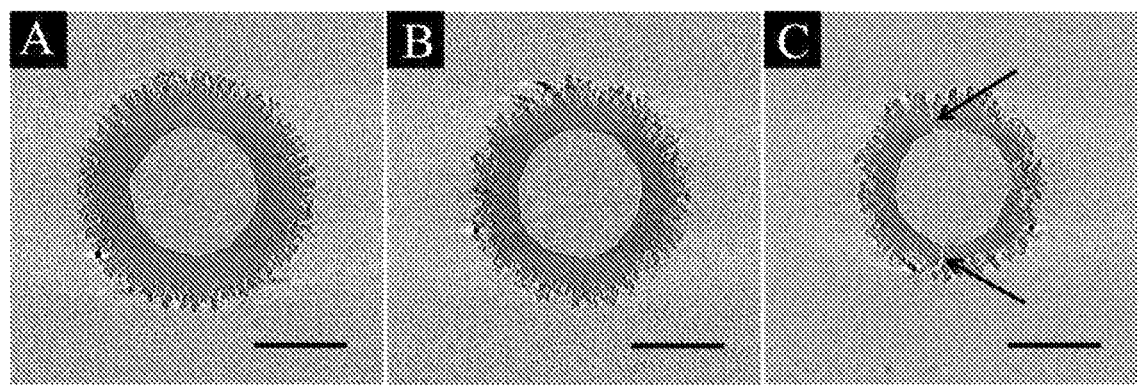
FIG. 11 shows Electron Tomography slices of the rough surface silica hollow spheres S-1.4 (A), S-1.0 (B), S-0.6 (C)

As shown in the TEM images shown in FIG. 10, the 'rod-like' rough structure can be clearly identified, however, the first silica layer beneath it is hardly revealed, even though a higher contrast appeared inside of the silica shell. To further explore the detailed structures of those rough silica hollow spheres, an electron tomography (ET) technique was utilized by taking a tilted series from +70° to 70° with an increase step of 1°. The tomograms were obtained by processing the tilted images with 10 nm Au fiducial alignment via IMOD. The tomogram slices referring to the middle part of the rough silica hollow spheres are shown as FIGS. 11 A-C. The silica shell observed from TEM images actually was composed of two layers, one relatively dense silica layer and another rough layer with 'rod-like' structures. The thickness of the dense silica layer decreased from 41 nm in S-1.4 to 31 nm in S-1.0, and even 19 nm in S-0.6. The decreasing thickness may result from the slower silica condensation rate with less TEOS amount addition. Interestingly, the relatively dense silica shell in S-1.4 (FIG. 11 A) and S-1.0 (FIG. 11 B) are both continuous without any pore structures connecting the hollow cavity. However, the one in S-0.6 showed several crevices with a width about 1-2 nm distributed on this layer (FIG. 11 C, black arrows), which provided transport channels for small molecules to access the inner hollow space.

Figure 12:
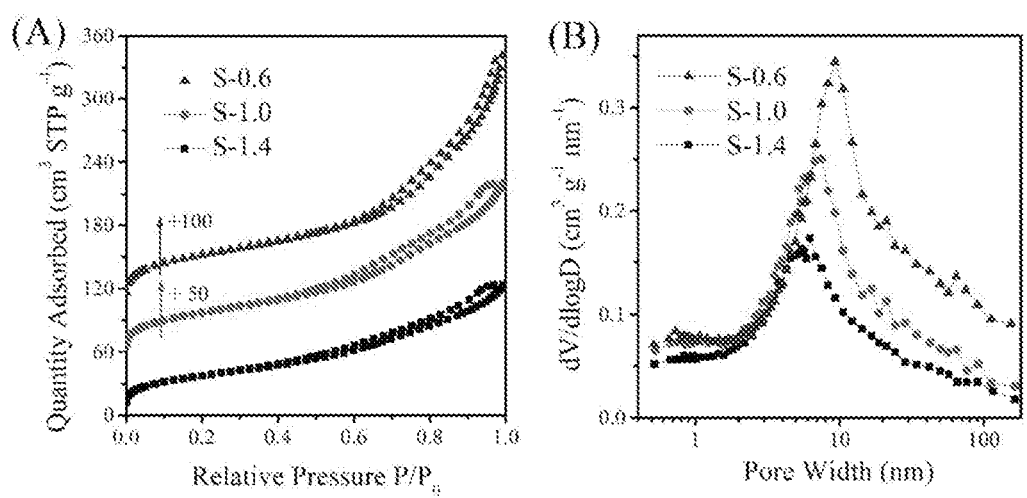
FIG. 12 shows $N_2$ sorption isotherm (A) and pore size distribution by BJH adsorption branch (B) of the rough silica hollow spheres made in example 2.
Figure 13:
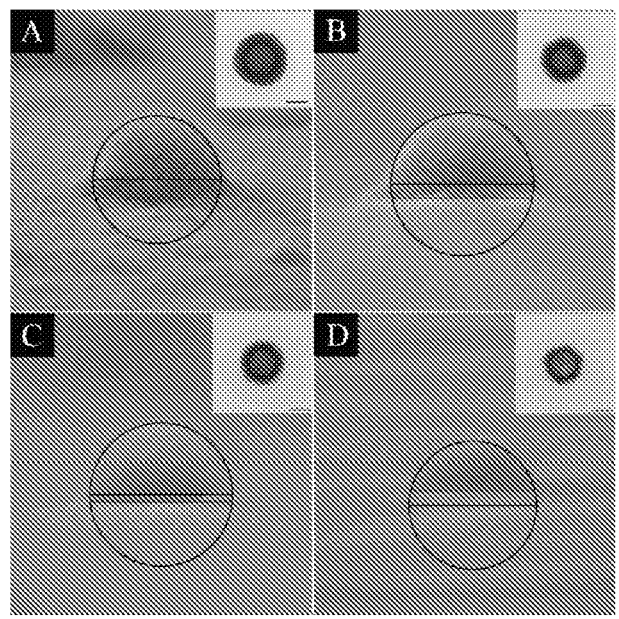
FIG. 13 shows SEM images for the contact angle test of smooth silica hollow sphere (A), S-1.4 (B), S-1.0 (C) and S-0.6 (D). Insert are the TEM images for its corresponding particles.

To further characterize this 'rod-like' structure and its distribution on the hollow sphere surface, a quantitative comparison was conducted. Due to the similar particle size of these rough hollow spheres, the distance between each silica 'rod' can indirectly represent its distribution density. Even though the interstitial geometry between the silica 'rods' is different from the traditional pore structures, its space can also be revealed by nitrogen sorption analysis and its pore size distribution (Ref Langmuir 1999, 15:8714; J. Colloid Interface Science, 2008, 317:442). As shown in FIG. 12A, the nitrogen adsorption and desorption results of these rough silica hollow spheres exhibited a type IV isotherm, with a hysteresis loop between 0.5-1.0 of $P/P_0$, indicating the existence of mesopore structures on the hollow sphere surface. The pore size distribution by BJH adsorption branch as shown in FIG. 12B indicated the distance between each silica 'rod' was enlarged from about 6.3 nm in S-1.4 to 7.5 nm in S-1.0, and to 9.3 nm in S-0.6. With enlarged distance between the silica 'rods', there are more of the spaces provided for the nitrogen molecules to condense, which will finally achieve a higher amount for adsorption (Ref Langmuir 1999, 15:8714). This is in accordance with the surface area and pore volume increase from 133 $m^2/g$ and 0.19 $cm^3/g$ of S-1.4, to 167 $m^2/g$ and 0.26 $cm^3/g$ of S-1.0, and 182 $m^2/g$ and 0.37 $cm3/g$ of S-0.6 with enlarged interstitial distance.

The introduction of surface roughness on various substrates has been achieved by a biomimetic approach in both microscale and nanoscale. The surface roughness results in enhanced hydrophobicity notwithstanding that the silica from which the nanoparticles are made is normally hydrophilic. However, the traditional characterization approach of water droplet contact angle results cannot be easily related to the contact angle of the individual particles, especially in nanoscale. Hence, a gel trapping technique (GTT), which is based on the proportional entrapping of individual nanoparticles on the oil-water surface, has been developed [Ref: Langmuir, 2004, 20:9594]. By spreading the particles on an oil-water surface and subsequent gelling of the water phase, the nanoparticles trapped on the water phase are then replicated and lifted up with poly(dimethylsiloxane) (PDMS) elastomer, which allows the particles partially embedded in the PDMS surface to be imaged with SEM [Ref Langmuir 2003, 19:7970]. This method allows the quantitative comparison of the surface hydrophobicity for individual nanoparticles with different surface roughness to correlate the interstitial distance of the rough structures and its hydrophobicity. To justify the enhanced surface hydrophobicity by rough structures, a smooth silica hollow sphere (FIG. 5A insert), with relatively dense silica shell thickness of 60 nm and no obvious mesopores on the shell, was selected as a control. As shown in FIG. 5, the smooth particle exhibited a contact angle of only 61°, while with rough structure emerged on the surface, the contact angle increased to 73° for S-1.4 and 86° for S-1.0. With even larger interstitial distance, the contact angle can reach 102°, indicating a hydrophilic silica material equipped with hydrophobic surface by the introduction of roughness, and increasing of surface hydrophobicity of the particles with enlarged distance between silica 'rods'.

To show the usefulness of the rough surface hollow silica spheres for the take-up of hydrophobic material, the rough silica hollow spheres were used for lysozyme adsorption. For comparison, smooth silica hollow sphere was employed as a control group, which only achieved 82 μg/mg. For the rough silica hollow spheres, an obvious enhancement for lysozyme adsorption was observed in FIG. 6, with the capacity for S-1.4 and S-1.0 increased to 358 and 408 μg/mg, respectively. Especially for S-0.6, the adsorption capacity can even reach as high as 641 μg/mg. The increasing adsorption capacity should be attributed to the larger interstitial distance, rising pore volume and enhanced surface hydrophobicity introduced by the surface roughness, as well as the volume provided by the accessible hollow central cores of the spheres.

Example 3—Delivery Systems for Use in Biological Systems

In biological systems, hydrophobic interactions are usually considered to be the strongest of all long-range non-covalent interactions. Hydrophobic interaction is beneficial for adsorption of biomolecules, improving interaction with cellular membranes increasing the uptake of nanoparticles for cellular delivery as well as tailoring the release rate of drugs. To generate nanoparticles with hydrophobic properties, the choices of hydrophobic composition or functionalization are among the convenient approaches. Hydrophobic material such as carbon nanotubes (CNTs) have shown great promise as nanoscaled vehicles for drug delivery, however one of the main concerns is the fact that CNTs could be hazardous to environment and human health which need further surface functionalization to reduce their intrinsic toxicity. Hydrophobic moieties such as alkanethiols and alkyl chains have been modified onto the surfaces of various nanoparticles including gold and silica to enhance the loading of hydrophobic drugs/protein and improve cellular delivery performance. However, chemically grafted hydrophobic groups tended to cause unwanted toxicity and pore blocking of nano-carriers. It is therefore a challenge to design a safe and efficient nanocarrier system employing an alternative approach.

In this example, surface roughness engineering was achieved by adding silica shell particles with smaller sizes (~13 or 30 nm in diameter) onto mesoporous hollow spheres of silica (MHS) with relatively larger sizes (~200 or 400 nm). The surface roughening creates the voids (the space between small shell spheres with a radius of R1) on the outer surface for air entrapment. The air pocket is significantly enlarged in this design because the internal spherical cavity with a radius of R2 (R2>>R1) is connected with the air through the mesopores in the silica shell. The repulsion of the trapped air in the void spaces towards water molecules provides the energy barrier against the wetting process because the hydroxyl groups in silica tend to adsorb water molecules as in the case of mesoporous hollow silica (MHS). Compared to rough solid Stöber (RSS) silica nanoparticles, rough mesoporous hollow spheres of silica (RMHS) provide more space to trap the air, leading to a higher energy barrier during the wetting process and thus more distinguished hydrophobicity. The nature of hydrophilic composition of RMHS provides a high loading capacity of the 'last resort' antibiotic vancomycin (VAN) while the hydrophobic property facilitates the controlled release of VAN and adhesion to bacteria, resulting in enhanced antibacterial efficacy, compared to free VAN and MHS-VAN.

Figure 14:
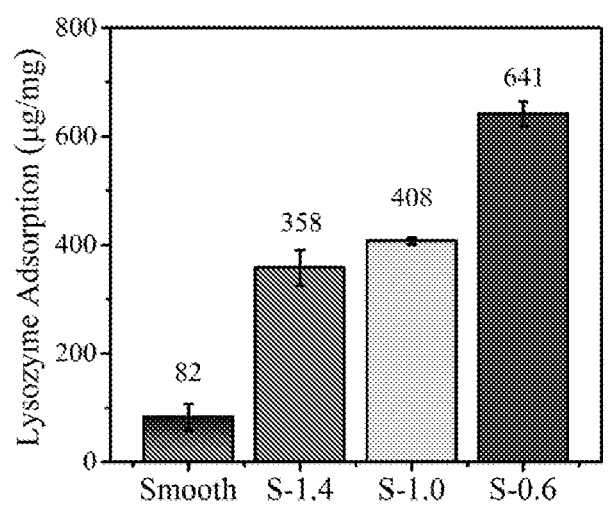
FIG. 14 shows lysozyme adsorption capacity of smooth and rough silica hollow spheres.

MHS nanoparticles were synthesized using a surfactant-directing alkaline etching strategy. RMHS was prepared by mixing positively charged MHS after amino group functionalization with negatively charged Stöber silica nanoparticles (~40 nm in diameter) followed by calcination. Scanning electron microscope (SEM) and high resolution transmission electron microscopy (HRTEM) images show that RMHS of 450 nm in average size have been successfully prepared with a uniform spherical morphology (FIG. 14a, 14c). The surfaces of RMHS are homogeneously decorated with 40 nm silica nanospheres, indicating the successful attachment of silica nanospheres to the surface of MHS. In contrast, MHS (FIG. 2b, 2d) has an average particle size of 350 nm. HRTEM images (FIG. 14c, 14d) clearly indicate the hollow core@porous shell structure of RMHS and MHS. The hollow core is ~230 nm in diameter and the porous shell is about 60 nm in thickness. SEM images show the hollow core of the nanoparticles with monodisperse morphology for both MHS and RMHS. The hydrodynamic size of MHS and RMHS was further measured by dynamic light scattering (DLS), which shows a size of 396 nm for MHS and 459 nm for RMHS, consistent with both SEM and TEM results. The distance between two neighboring silica nanospheres is measured at around 30 nm and the gap between them provides space for the air entrapment.

Both MHS and RMHS exhibited typical type-IV isotherms with an H2-type hysteresis loop, indicating the existence of well-defined mesopores. The pore size distributions calculated from the adsorption branches using the Barrett-Joyner-Halenda (BJH) method showed that both samples have uniform mesopores centered at 3.5 nm. RMHS has a relatively lower surface area compared to MHS (342 vs. 427 $m^2$ $g^{-1}$) because the shell particles are solid. The higher pore volume of RMHS (0.46 vs 0.31 $cm^3$ $g^{-1}$ of MHS) is mainly attributed to the inter-particle packing voids as reflected by the capillary condensation step which occurred at relative pressure ($P/P_0$) higher than 0.95. Surface charge measurement by z-potential showed that both RMHS and MHS were negatively charged to a similar degree. Both samples have pure silica in composition as confirmed by Fourier transform infrared spectroscopy (FTIR), showing characteristic peaks for physisorbed water (—OH) at 1620 $cm^{-1}$, silanol group (Si—OH) at 790 $cm^{-1}$, as well as siloxane group (Si—O—Si) at 1062 and 449 $cm^{-1}$.

The hydrophobicity of the nanoparticles was observed by the dispersion of MHS and RMHS in a mixed solvent of water/diethyl ether. RMHS preferentially rests at the bottom of the diethyl ether layer (a hydrophobic solvent) while MHS directly disperses in the water layer (a hydrophilic solvent) even without gentle shaking. RSS was also showing similar behavior as RMHS in the water/diethyl ether layer. This occurred due to the competition between the affinity of Si—OH towards water molecules and the repulsion of the trapped air in void spaces towards both oil and water molecules (as presented in FIG. 1). Thermal gravimetric analysis (TGA) profiles presented a small weight loss of 0.9% below 200° C. for RMHS while 7.2% for MHS which can be attributed to the evaporation of moisture. The TGA results indicate that the introduction of surface roughness makes RMHS more hydrophobic and thus it absorbs less moisture from the atmosphere than MHS.

A dye (rose Bengal, RB) adsorption method was also employed to quantitatively determine the relative hydrophobicity of nanoparticles. A plot of partitioning quotient (PQ) versus nanoparticle surface area per millilitre was constructed for RMHS, MHS and RSS. The slope of this plot is proportional to the relative hydrophobicity of nanoparticles. Compared to RSS with the slope of $0.000675 \times 10^{-9}$ mL $\mu m^{-2}$, RMHS yielded higher slope value of $0.00106 \times 10^{-9}$ mL $\mu m^2$, indicating higher hydrophobicity of RMHS compared to RSS. MHS on the other hand showed the lowest slope with no significant value suggesting a hydrophilic nature.

Figure 15:
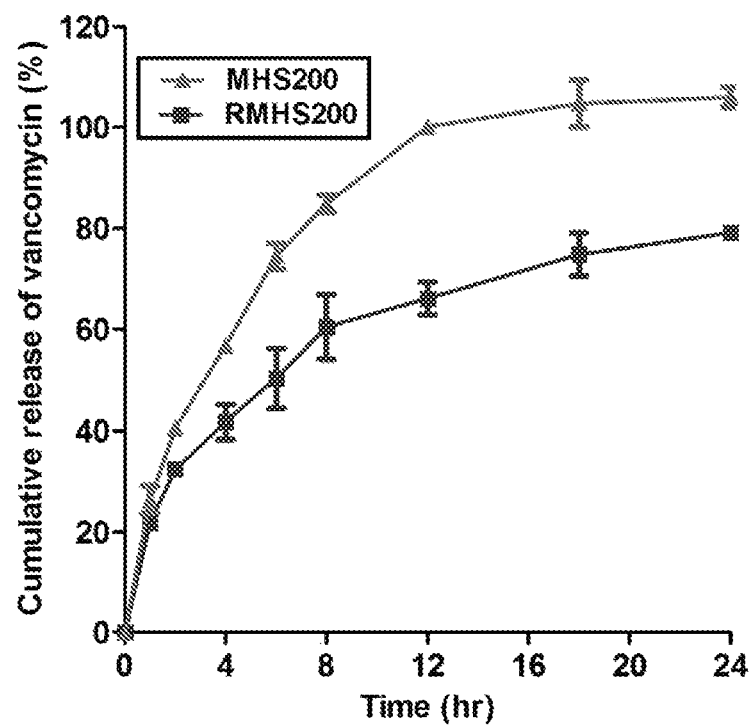
FIG. 15 shows the uptake and release behaviour of the nanoparticles towards hydrophobic and hydrophilic molecules. a) Loading capacity of MHS and RMHS on drug and different proteins, b) uptake rate of DR1; The solutions containing particles were pre-treated with sonication before adding the proteins or drugs for loading; c) the release behaviour of VAN for 400 nm particles and d) The release behaviour of VAN for 200 nm particles. The error bars reflect the standard deviation of the measurements.

RMHS and MHS were used in the adsorption of three hydrophobic proteins including RNase A (RNASE), insulin (INS) and lysozyme (LYS) a hydrophobic dye, disperse red 1 (DR1) and a hydrophobic drug, griseofulvin (GRIS). As shown in FIG. 15a, a higher loading capacity was achieved exclusively for five sorbates by RMHS than MHS. Compared to MHS, a faster adsorption rate of DR1 (FIG. 15b) and LYS was also observed when comparing RMHS to MHS. These results indicate that enhanced surface hydrophobicity of nanoparticles favours higher and faster loading of hydrophobic molecules. The loading capacity of RSS towards LYS was also measured as 25.9 mg $g^{-1}$. Compared to that of RMHS (263.1 mg/g), the much lower LYS loading amount of RSS can be attributed to its solid nature.

To further understand the role of air which induced RMHS hydrophobicity, the adsorption capacity of RMHS towards LYS was conducted in solutions after removing air bubbles under a vacuum condition. The adsorption amount of the LYS on RMHS was found to be reduced by 37.3% (from 263.1 mg $g^{-1}$ to 172.1 mg $g^{-1}$), comparable with the adsorption capacity of MHS (161.5 mg $g^{-1}$). An additional experiment was conducted by eliminating the pre-sonication process to retain most of the air trapped by the nanoparticles. Higher loading of LYS was achieved by RMHS without sonication with 27.5% increment compared to the adsorption using RHMS subject to pre-sonication steps in FIG. 15a. These results confirmed the role of air as the hydrophobic solvent on the RMHS structure which subsequently improves the adsorption for protein. In contrast, surface roughness has no influence on the loading capacity of a hydrophilic molecule, VAN, as shown in FIG. 4c. Similar loading value was achieved for both MHS and RMHS with this hydrophobic molecule. However, the hydrophobic property of RMHS enabled sustained release behaviour of VAN up to more than 36 h relative to 100% release at 8 h for MHS (FIG. 15c).

The size of the core nanoparticles with similar morphology can be further finely tuned with the same preparation method. The inventors have successfully prepared MHS and RMHS with an average core size of 200 nm and 13 nm shell particles size named as MHS200 and RMHS200. Both nanoparticles have similar surface morphology compared to the larger particles (MHS and RMHS) as shown by TEM and SEM images. MHS200 and RMHS200 have slightly smaller pore size (3.4 nm) and relatively higher pore volume (0.38 $cm^3$ $g^{-1}$ for MHS200 and 0.62 $cm^3$ $g^{-1}$ for RMHS200) compared to the larger sized particles.

The use of nanoparticles as a delivery vehicle for antibiotics provides a promising strategy through prolonged drug circulation half-life, increased availability of drugs interacting with membrane molecules and promoted sustained drug release. VAN is an antibiotic useful for the treatment of a number of bacterial infections since it inhibits the cell wall synthesis in susceptible bacteria. To demonstrate the antibacterial efficacy of VAN delivered by the surface engineered materials, drug loaded nanoparticles were incubated with *Escherichia coli* (*E. coli*). Nanoparticles with a size of 200 nm (MHS200 and RMHS200) were chosen in this study because the screen test showed that compared to larger particles (~400 nm), smaller ones exhibited higher bacterial toxicity effect. The in vitro antibacterial activity of VAN, MHS200-VAN and RMHS200-VAN was evaluated by monitoring the optical density (OD) at 600 nm of a bacterial suspension. *E. coli* ($1 \times 10^6$ CFU mL$^{-1}$) was incubated in Luria-Bertani (LB) medium in a 1.5 ml centrifuge tube at various concentrations of VAN for 18 h. The minimum inhibitory concentration (MIC) value of free VAN towards *E. coli* was observed at 25 μg mL$^{-1}$ (FIG. 16a). This value reduced to 20 μg ml$^{-1}$ for RMHS200-VAN which is lower than the dosage used with VAN conjugated MCM-41 (200 μg ml$^{-1}$) in in-vitro *E. coli* culture at 18 h. In a separate experiment, MHS200-VAN, RMHS200-VAN and free VAN with the same VAN content of 25 μg ml$^{-1}$ were incubated with $1 \times 10^6$ CFU mL$^{-1}$ *E. coli* in LB media and OD was measured as a function of time. It was observed that RMHS200-VAN maintained 100% inhibition throughout 24 h. However, re-growth of bacteria as evidenced by increases in OD was observed in both MHS200-VAN and free VAN groups after 18 h (FIG. 16b).

It was reported that the re-growth of bacteria exposed to VAN may occur if inadequately inhibited bacteria synthesize new peptidyglocan to override the antibacterial effect of VAN. The 100% inhibition of *E. coli* even at 24 h in the case of RMHS200-VAN should be attributed to two advantages coming from the nanoparticle design: 1) the rough surface particles have a higher efficacy compared to their smooth counterparts; and (2) the hydrophobic nature of RMHS200 which leads to a sustained release of VAN compared to MHS200 (FIG. 16d), similar to the larger sized nanoparticles (FIG. 16c). Eventually the effective time window of the drug is increased.

Figure 16:
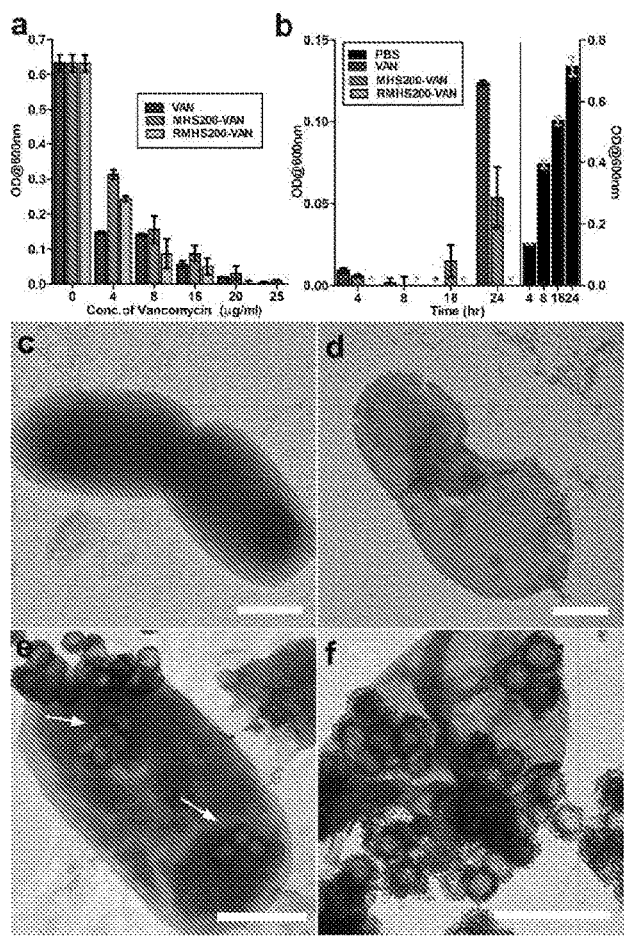
FIG. 16 shows antibacterial performance. a) Dose dependent antibacterial activity against *E. coli* of RMHS200-VAN, MHS200-VAN and free VAN cultured for 18 h, using PBS as a control. b) Time dependent antibacterial study at the VAN dosage of 25 mg ml$^{-1}$ up to 24 h. c) TEM images of *E. coli* treated in PBS, d) *E. coli* treated in VAN, e) *E. coli* treated in MHS200-VAN and f) *E. coli* treated in RMHS200-VAN at the dosage of 25 mg m$^{-1}$ for 18 h. * indicated 100% inhibition. The error bars reflect the standard deviation of the measurements. Scale bar=500 nm (see example 3).

To provide direct evidence on the antibacterial efficacy of nanoparticles, TEM was employed to observe the morphology of *E. coli* cultured at 24 h (FIG. 16(c-f)). For the untreated group (FIG. 16c), the typical cylindrical morphologies of *E. coli* remained intact. Compared to the untreated group, VAN treated bacteria showed damage of the bacterial membrane (FIG. 16d-f). For MHS200-VAN, MHS200 was found in the bacterial membrane (FIG. 16e) and severe damage of the wall/membrane of *E. coli* (FIG. 16f) was clearly observed. The cell cytotoxicity of MHS200 and RMHS200 to normal human dermal fibroblast (HDF) was also assessed by the MTT assay. No significant cytotoxicity of both nanoparticles even at a concentration of up to 500 μg/mL was observed, providing evidence of excellent bio-inertness and safety of the materials as the carrier system.

In conclusion, this example shows that the inventors have successfully prepared novel nanoparticles with a hydrophilic silica composition but having hydrophobic properties through surface roughness modification, which show higher loading capacity of hydrophobic molecules and sustained release for hydrophilic drugs compared to their counterparts with a smooth surface. The fundamental understanding gained from this study provides a new strategy for the development of nanocarriers with safe composition and high performance in widespread drug delivery applications.

Example 4—Preparation of Carbonaceous Nanoparticles

Figure 17:
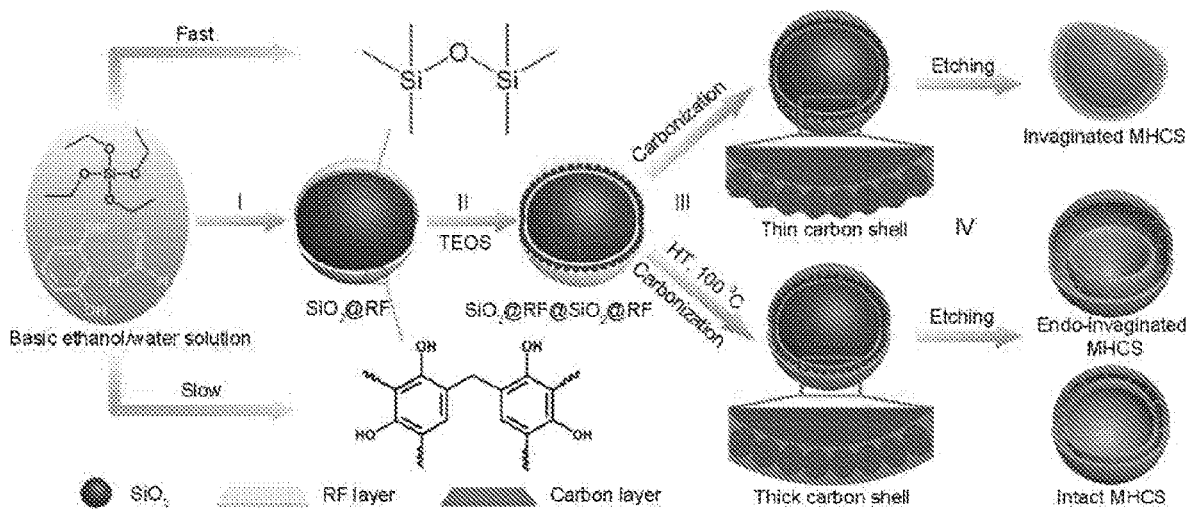
FIG. 17 shows a schematic illustration for the synthesis of invaginated, endo-invaginated and intact MHCSs through a sequential heterogenous nucleation mechanism in accordance with an embodiment of the fourth aspect of the invention.

In this example, a new sequential heterogeneous nucleation (SHN) pathway to prepare self-organized colloidal carbon nanoparticles with controllable mesostructures and morphologies in the absence of structure directing agents is reported. The SHN concept is schematically illustrated in FIG. 17. The synthesis is carried out in an ethanol/water system with NH$_3$.H$_2$O as the catalyst, simply using tetraethyl orthosilicate (TEOS), resorcinol and formaldehyde (RF) as precursors. In step I when TEOS and RF precursors are mixed together, Stöber spheres are formed through a homogenous nucleation process due to the relatively faster condensation rate compared to the RF system. Once the silica spheres are formed, the RF precursors preferentially condense on the silica surface through heterogeneous nucleation. In order to tune the wall structure, TEOS is introduced again in step II, which forms uniformly distributed silica nanoparticles on the RF shell surface through a subsequent heterogeneous nucleation process. The residual RF oligomers further condense on the top of silica nanoparticles to create a second RF layer. After carbonization with or without hydrothermal treatment (step III) under inert atmosphere followed by the removal of silica (step IV), mesostructured hollow carbon spheres (MHCS) with a bilayered structure are obtained. By controlling the thickness of carbon/silica shells, the bilayered morphology (invaginated, endo-invaginated or intact spheres) and mesopore size can be finely regulated.

Figure 18:
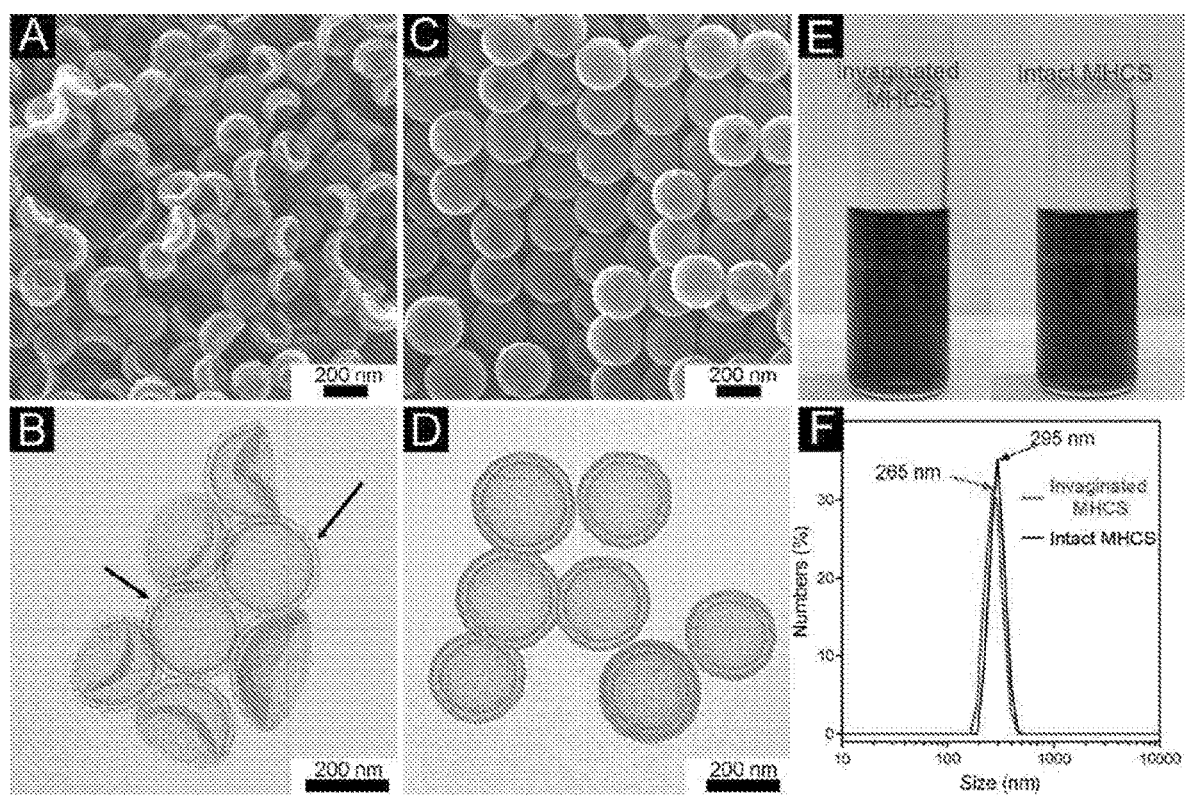
FIG. 18 shows SEM (A, C) and TEM (B, D) images of invaginated and intact MHCSs, respectively. Digital images (E) of two MHCSs dispersed in aqueous solutions showing the Tyndall effect and the particle size distribution curves (F) by DLS measurement.

From the scanning electron microscopy (SEM) images presented in FIG. 18 (A,C), MHCS prepared without hydrothermal treatment in step III exhibit an invaginated spheroidal morphology, much like a deflated balloon where one side of the sphere becomes enfolded towards the other. Transmission electron microscopy (TEM) images of the invaginated MHCS show a clearly bilayered and hollow internal structure (FIG. 18B). When MHCS are prepared with hydrothermal treatment, an intact spheroidal morphology is obtained as shown by the SEM image (FIG. 18C). TEM observations for these particles also show a bilayered concentric spherical structure (FIG. 18D).

Invaginated and intact MHCS exhibit uniform outer diameters of 250 and 270 nm, respectively. Moreover, both particles disperse well in aqueous solution and produce the characteristic Tyndall effect commonly observed for monodispersed colloidal suspensions (FIG. 18E). Dynamic light scattering (DLS) measurements reveal a hydrated particle size of 265 and 295 nm for invaginated and intact MHCSs, respectively (FIG. 18F). The narrow size distributions and low polydispersity index (PDI of 0.1) for two samples indicate both MHCS possess highly uniform particle size and excellent water dispersibility. High resolution SEM images reveal highly porous, rough external surfaces with open-pore entrances for the invaginated MHCS. Intact MHCS on the other hand, exhibit relatively smooth and continuous surface morphology.

For three-dimensional (3D) nano-objects with complex internal structures such as MHCS, investigation by conventional TEM may provide misleading information. This is because TEM images provide the collective structural information over a certain thickness and merge it into a 2D projection. For example, the fine structures between the inner and outer layers are not clear. Moreover, it seems that two spheres shown in FIG. 18B (indicated by arrows) are not invaginated, although this effect could result from the electron beam passing perpendicular to the plane of invagination. Electron tomography (ET) is a rapidly developing technique for the advanced 3D imaging of complex structures, which allows virtual reconstruction of a material's internal structure using 3D models built from a series of 2D slices (19, 20).

Figure 19:
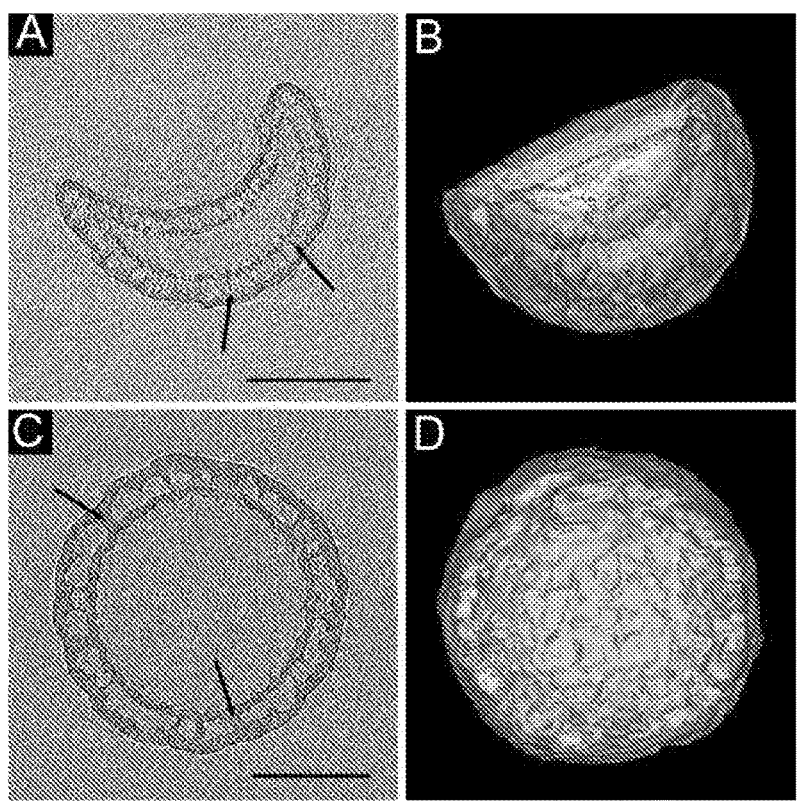
FIG. 19 shows ET slides of invaginated MHCS (A) and intact MHCS (C), ET reconstruction of invaginated MHCS (B) and intact MHCS (D). Scale bars are 100 nm.

We used the ET technique to study the detailed structures of MHCS. A series of tilted images was taken in the range of +70 to −70° with increments of 1°. Using this technique, one can clearly observe the invaginated MHCS particle apparently changing from an invaginated to an intact spherical structure. This highlights the ambiguity of the data provided by conventional TEM alone and confirms the importance of ET characterization for materials with complex and asymmetrical architectures. To observe the detailed internal structures of MHCS, electron tomograms were generated from two perpendicular tilting series using IMOD software (21). The ET slice which cuts perpendicular to the invagination face of the MHCS (FIG. 19A) exhibits a clearly bilayered, crescent moon-like morphology. The inner and outer layers are linked by thin carbon bridges of approximately 1-2 nm in thickness (indicated by black arrows). In contrast, a tilt-series of the intact MHCS reveals a complete spherical morphology throughout the rotation (data not shown). The ET slide in FIG. 19C shows a full moon-like morphology for the intact MHCS, where the two concentric layers are linked by more substantial carbon bridges with approximately 4-5 nm in thickness.

The invaginated and intact samples also differ noticeably in thickness and the degree of continuity of inner and outer shells. The outer layers of the invaginated and intact samples appear relatively continuous with an average thickness of 6 and 12 nm respectively, however the inner layer of the invaginated structure shows numerous defects and interruptions which form a more fragile and discontinuous inner shell when compared to the intact structure. The average sizes of the void spaces between two layers measure approximately 15 and 20 nm radially from the inner to the outer shell for the invaginated and intact MHCS, respectively. Digitally reconstructed structures for two MHCS with inner shells in orange and outer shells in yellow are shown in FIGS. 19B and 19D, respectively. Invagination of both the inner and outer shells can be observed for the invaginated MHCS while spherical morphology is seen for the intact MHCS, which is consistent with the morphological observations from TEM and SEM. Moreover, carbon bridges linking the inner and outer shell can also be observed for both invaginated and intact MHCS.

Nitrogen sorption studies for both invaginated and intact MHCS show type-IV adsorption isotherms. The BJH pore sizes calculated from the adsorption branch indicate pore sizes of 15.9 and 18.0 nm for the invaginated and intact MHCS, respectively. These pore sizes correspond closely with the measured interlayer distance between the inner and outer shells observed in ET and TEM micrographs, suggesting this confined interlayer space is responsible for the BJH pore size distribution. The BET surface area and pore volume of invaginated MHCS (1032 m2 g-1 and 2.11 cm3 g-1, respectively) are slightly higher than those obtained for the intact MHCS (880 m2 g-1 and 1.44 cm3 g-1, respectively), which may be attributed to thinner shells and thus the increase in bulk-to-surface ratio for the more solidly constructed intact MHCS. The X-ray photoelectron spectra (XPS) show that only peaks from C1s (~285 eV) and O1s (~534 eV) are detected, revealing the major components of both invaginated and intact MHCSs are carbon and oxygen (22). The mass percentage of carbon and oxygen are calculated to be 92.9% and 7.1%, respectively. The X-ray diffraction (XRD) patterns reveal the amorphous nature of MHCS.

In order to understand the formation mechanism of MHCS, we systematically studied the nucleation and growth processes of silica-RF particles as a function of time. Since both TEOS and RF can independently polymerize under the same conditions to form uniform solid particles (FIG. 20, curve I and II), their individual reaction kinetics was first investigated. Under the synthesis conditions utilised, the polymerization of TEOS results in formation of silica particles within 15 minutes (m), consistent with the typical induction period commonly observed in Stöber sphere formation (23). These spheres then rapidly increase in size up to 2 h, after which particle size is relatively consistent. RF polymerization under the same conditions on the other hand, forms spheres with slower growth. The formation of some irregular RF polymer nucleates is observable at 1 h, which continue developing into spherical particles by 2 h. The RF spheres increase in size relatively rapidly from 2 to 6 h followed by a slower growth region till 12 h. From curve II it can be inferred free RF oligomers persist in the synthetic system at 12 h.

Figure 20:
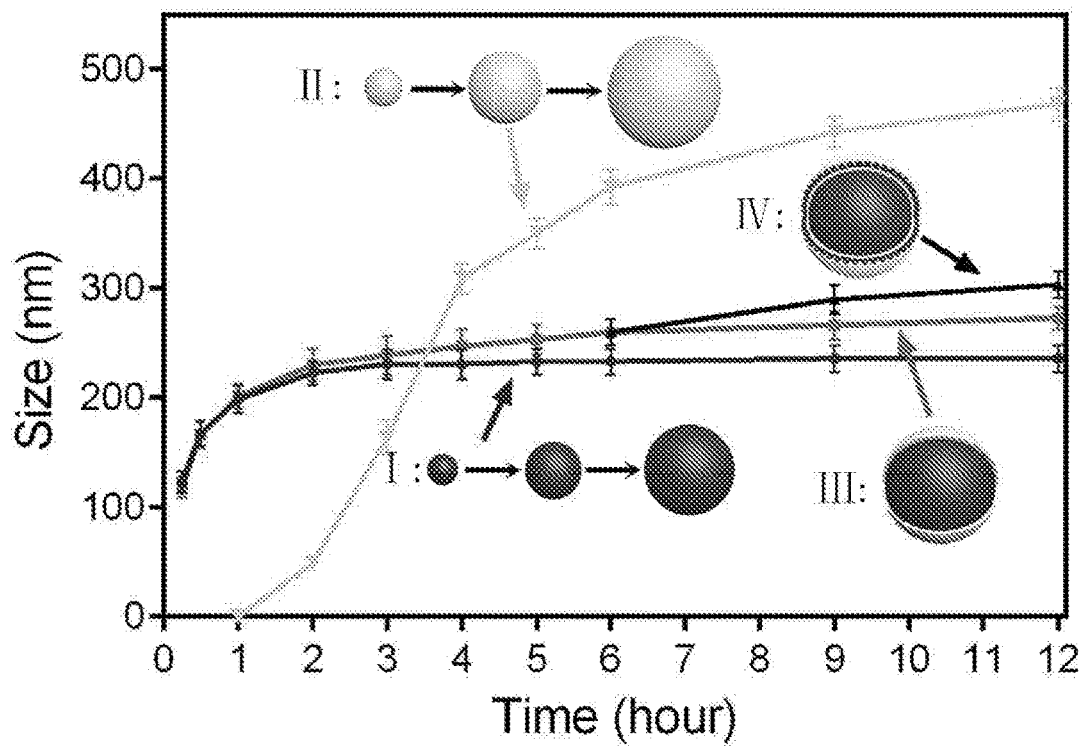
FIG. 20 shows particle sizes of pure silica (curve I), pure RF (curve II), silica@RF (curve III) and silica@RF@silica@RF (curve IV) as a function of reaction time.

When TEOS and RF are added simultaneously, FIG. 20 curve III reveals that the particle size initially (up to 1 h) follows the same trend as the pure silica system with only silica particles are formed. After 2 h the particle sizes increase gradually to 250 nm at 12 h, forming silica@RF core-shell structures with increasing RF shell thickness as a function of time. No evidence of solid RF spheres nor solid carbon spheres after carbonization/silica etching can be found, indicating that the RF polymerization system has been changed from homogeneous to heterogeneous nucleation on the surface of silica cores, consistent with classical nucleation theory that the free energy barrier for heterogeneous nucleation on a surface is considerably lower as compared to homogeneous nucleation. However, this approach leads to hollow carbon spheres with only microporous walls, which has little control over the morphology and mesostructures of final products and thus limited applications.

When TEOS is introduced in step II at a carefully chosen time-point of 6 h, TEM was used to monitor the structural evolution over the following 2 h. From TEM images of samples after calcination in air, it can be seen that a secondary population of silica nucleus appears on the surface of silica@RF particles within 15 m after the second TEOS addition. The secondary silica nanoparticles increase in size from ~5 nm at 15 m up to ~10 nm at 30 m before merging together to form a relatively continuous interlinked silica shell with a radial thickness of 18 nm at 2 h. After secondary TEOS addition, the particle size steadily increases (FIG. 20, curve IV) relative to the silica@RF particles shown in curve III, achieving an additional 30 nm in diameter after 12 h of growth. TEM data confirm the absence of any solid silica nanoparticles in the final products. The above observations indicate that the RF layer of silica@RF particles formed in step I triggers a subsequent heterogeneous nucleation of TEOS. Due to the slower polymerization behavior of RF system, the remaining RF precursors preferentially nucleate on silica surface. The sequential heterogeneous nucleation of two polymerisable systems and their interplay gives rise to an interpenetrating silica-RF composite shell structure. Removing silica in the core and shell after carbonization results in the final structures of MHCS.

The ET results of fine structures of MHCS are in accordance with the SHN mechanism. The bridges in between two carbon layers come from the intergrowth of RF with secondary silica nanoparticles. Hydrothermal treatment favors further condensation of RF system, leading to thicker bilayers as well as bridges and eventually intact MHCS. The invaginated MHCS with exposed porous surface are formed due to the thinner RF layers and bridges when hydrothermal treatment is not used in step III.

The SHN mechanism can recur over additional nucleation cycles. As a demonstration, a third addition of silica and RF precursors was introduced to the system. The resulting triple-layered MHCS structures are consistent with another cycle of heterogeneous nucleation. The added TEOS heterogeneously nucleates on the RF surface, forming an additional population of silica nanoparticles, followed by heterogeneous nucleation and growth of RF over silica. The use of SHN pathway under the same polymerization conditions for multiple cycles provides scope for the design of nanomaterials with elegant structures.

Judicious selection of time-points for the addition of TEOS in step II can determine the form of the final structures. When TEOS was added earlier (at 3 h time point instead of 6 h), no obvious bilayered structures were observed for both the invaginated and intact carbon particles. Instead, the structures exhibit single layered mesoporous carbon shells. When TEOS was added at 24 h, only hollow microporous carbon structures with thickness of 15 nm are obtained. These results demonstrate that carefully controlling the polymerization kinetics and elaborately regulating the nucleation process of TEOS and RF precursors in sequence enables the formation of bilayered MHCS.

To investigate the parameters influencing the invagination of hollow particles, we prepared a series of single layered hollow carbon spheres with controlled wall thicknesses. Wall thickness was controlled from 5 to 16 nm via the increase in stirring time from 6 to 36 h (step I in the scheme). The results clearly demonstrate that when the thickness of single layered hollow carbon sphere is as thin as 5 nm, most particles show invaginated morphology. With an increased thickness to 8 nm, only a small number of invaginated spheres can be observed, while an increase to 13 nm yields only intact spheres. This study demonstrates that the thickness of carbon layer plays a crucial role in controlling the invaginated or intact morphologies of the final products.

The distance between the shells was tuned from 7 to 27 nm by increasing the amount of TEOS from 0.5 to 2.5 ml added in step II. All the samples prepared without hydrothermal treatment exhibit invaginated morphology while the samples with hydrothermal treatment exhibit intact spherical morphology. The pore sizes, BET surface areas and pore volumes of the samples calculated from $N_2$ sorption are consistent with the results obtained from TEM measurements. The general trend is that the samples without hydrothermal treatment exhibited much higher surface areas and pore volume than those with hydrothermal treatment, consistent with what we observed before. Moreover, the greater the distance between the shells, the higher the observed surface area and pore volume. This can be ascribed to the enlarged mesoporous interlayer region in samples with large interlayer spacing. The corresponding silica templates show increased sizes and continuity of silica shells with the increasing amount of TEOS added.

Figure 21:
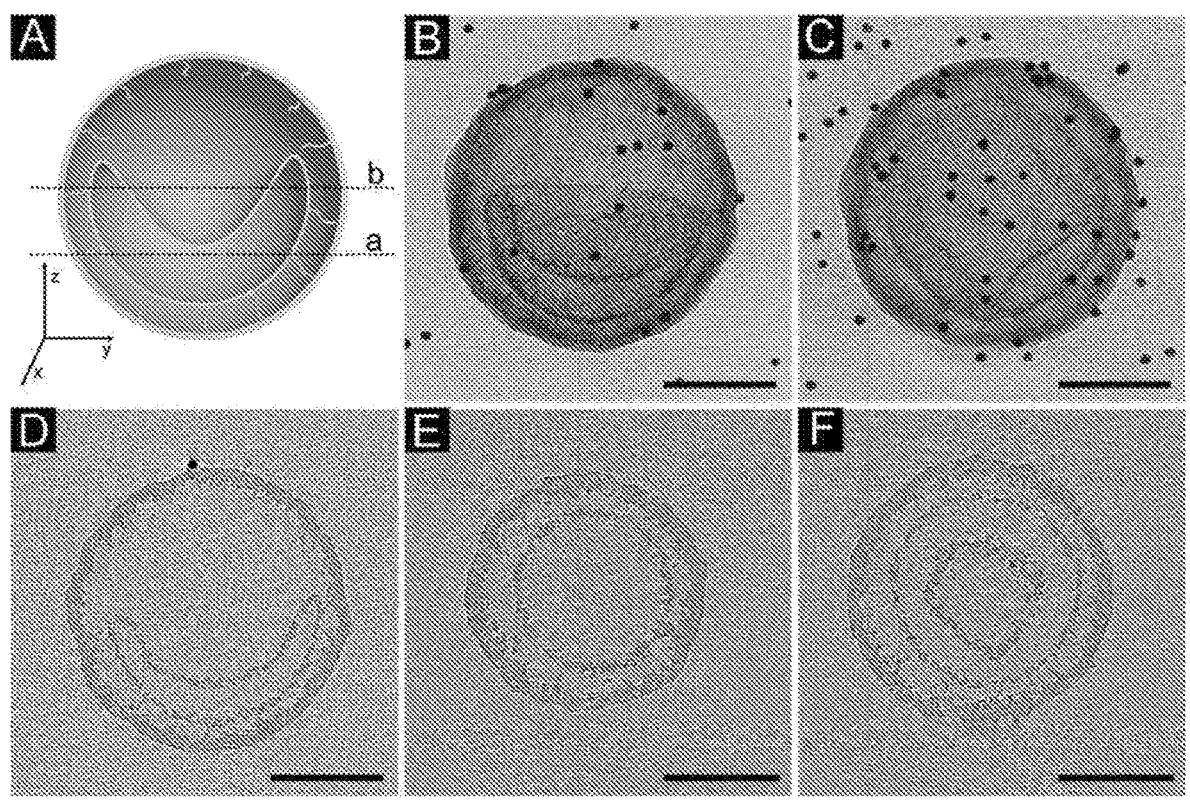
FIG. 21 shows MHCS with inner shell invaginated and outer shell intact. Diagram (A) shows the internal structure of the particle relative to the XYZ orientation. Tilted TEM images (B and C). Slice (D) cuts the YZ plane in the centre of the particle while silde (E) and slice (F) cut the XY plane at position a and b as indicated in diagram (A), respectively. Scale bars are 100 nm.

Notably, when the interlayer spacing is enlarged to 27 nm and after hydrothermal treatment, an unprecedented structure with the inner layer invaginated while the outer layer remains intact (so called endo-invaginated structure) is obtained (FIG. 21A). FIGS. 20B and 20C show two TEM images recorded along x- and z-axis (parallel and perpendicular to endo-invaginated plane), respectively. The ET slice shown in FIG. 21D reveals the cross-sectional crescent and spherical morphology of the inner and outer layers respectively along the yz plane right in the middle of the endo-invaginated structure. Two additional ET slices are given along the xy plane (FIGS. 21E and 21F) at z-height of a and b as indicated in FIG. 21A, respectively, showing two concentric rings and three concentric rings accordingly. Some carbon bridges can be observed connecting the outermost ring to the middle ring (FIGS. 21E and 21F). The middle ring however, has no observable bridges connecting the inner-most ring, indicating that these two surfaces originally coming from the inner sphere are not fused. These distinct structure features would be impossible to obtain using conventional characterization techniques other than ET.

The invagination of the inner shell can be ascribed to the formation of a thick and continuous silica layer during step II, which limits the interpenetration of RF and thus decreases the thickness and density of the carbon bridges. It is also noted that shell thickness of the outer sphere is thicker compared to that of the inner invaginated one (FIGS. 21D-21F) attributed to the hydrothermal treatment. With reduced support from bridging between the outer and inner shell, the more fragile inner sphere with thinner walls partially detaches and collapses away from the thicker, intact outer shell, forming the unique endo-invaginated MHCS.

We further tested the application of MHCS for lysozyme adsorption. For both invaginated and intact particles, around 75% of the saturation adsorption can be achieved within 10 minutes, suggesting fast adsorption kinetics towards lysozyme. The maximum adsorbed amount of lysozyme on the invaginated particles is around 1250 $\mu g \cdot mg^{-1}$ after 6 h, showing the highest adsorption capacity towards lysozyme compared to previous reports. The fast adsorption rate and high adsorption capacity should be attributed to the large entrance size, high surface area and the hydrophobicity of the invaginated MHCS.

This example demonstrates that colloidal carbon particles with unprecedented structures (invaginated, endo-invaginated and intact bilayered morphologies) have been designed via a sequential heterogeneous nucleation pathway through the self-organization of two polymerizable systems. This SNH mechanism defines the recurring heterogeneous nucleation cycles through which nanostructured interpenetrating composites can be self-organized and the structure, morphology of colloidal carbon nanoparticles can be precisely adjusted.

Example 4: Demonstration of Enhanced Adhesion to Bacterial Cell Walls

Figure 22:
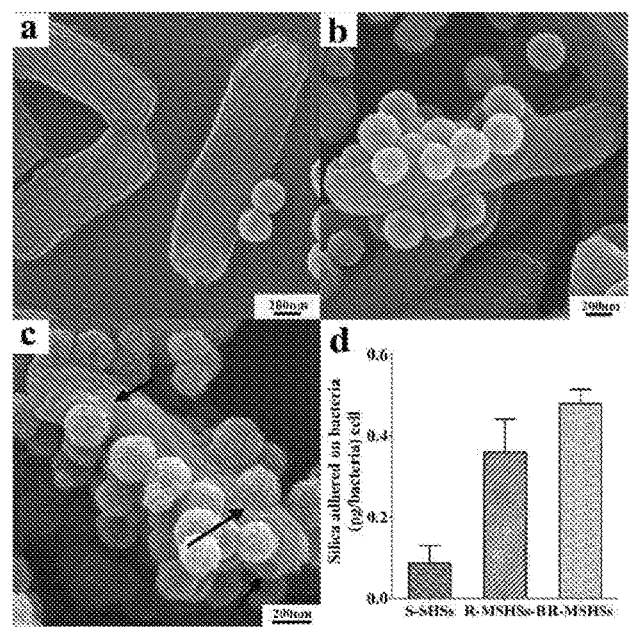
FIG. 22 shows SEM images of S-SHSs (a), R-MSHSs-B (b) and R-MSHSs (c) adhered on *E. coli* surface, and quantitative analysis of silica content adhered on bacteria from ICP-OES (d), as described in Example 4.

*E. coli*, a typical gram-negative bacteria, was employed and incubated with silica hollow spheres (concentration of 100 $\mu g \cdot mL^{-1}$) in Luria Broth (LB) media. The particle-bacteria adhesion of MSHS-SS and MSHS-RS particles was compared to demonstrate the effect of the rough silica surface by direct observation using electron microscopy after bacteria fixation and staining. As shown in FIG. 22a, *E. coli* exhibits intact rod-like morphology with fewer MSHS-SS particles adhered to the bacterial surface compared to MSHS-RS-B (FIG. 22b) and MSHS-RS particles (FIG. 22c). To be noted, some of MSHS-RS particles are partially engulfed into the bacteria cell wall, leaving a semi-spherical dent on the bacteria surface upon detachment (FIG. 22c, identified by black arrows). The engulfment process is typically related to the strength of the attractive cell membrane-particle interactions, an indication of enhanced adhesion between MSHS-RS particles and the bacteria cell wall. In contrast, the smooth surface of MSHS-SS particles provides limited contact area for interfacial interaction, resulting in less particles adhered on bacteria surface. Moreover, the electrostatic repulsion between both negatively charged silica nanoparticles and bacteria surface hinders their interaction as well. It is favorable to enhance the electrostatic attraction towards bacteria for silica nanoparticles by amine modification. However, the unwanted toxicity induced by the amine groups remains a concern. Here, by engineering surface roughness, MSHS-RS particles show enhanced bacterial adhesion properties, which may be attributed to the multivalent interactions induced by their surface spikes when contacting with the hairy bacteria surface, resulting in strong adhesion via a large number of contacts.

To quantitatively analyze the silica amount adhered on the bacteria surface, the bacteria cultured with the silica particles were filtered through a 450 nm-pore filter membrane. Extensive washing was applied to remove the isolated particles in the solution. Bacteria-free samples were also analyzed as a control and to eliminate the interference from aggregated silica particles. The ICP results (FIG. 22d) show that less than 0.1 pg of MSHS-SS particles adhere on each bacterial cell surface, whereas, 0.36 pg of MSHS-RS-B and 0.48 pg of MSHS-RS particles remain on each bacteria.

Example 5: Formulation with Lysozyme

Figure 23:
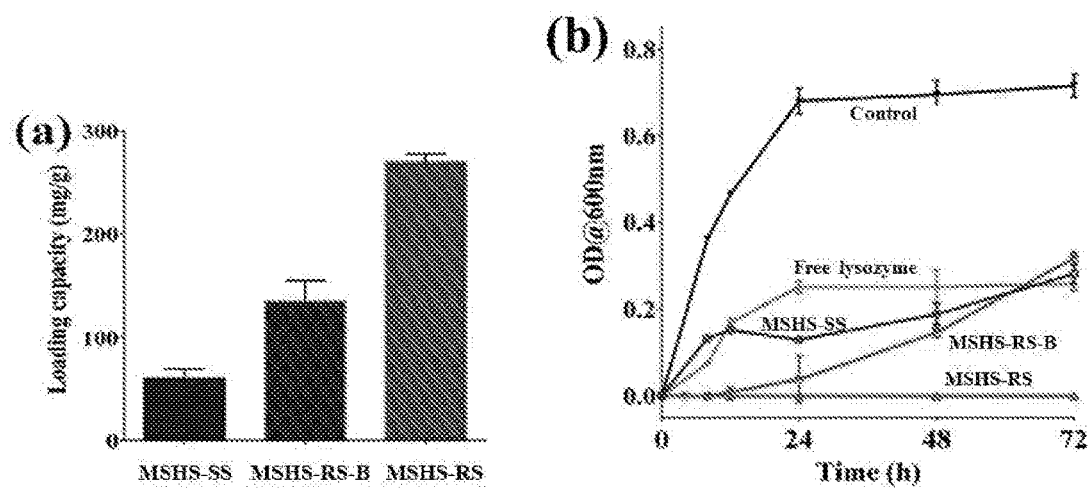
FIG. 23 shows (a) Lysozyme loading, (b) time dependent antibacterial activities of free lysozyme and lysozyme loaded silica particles at the lysozyme dosage of 700 ng/mL, as described in example 5.
Figure 24:
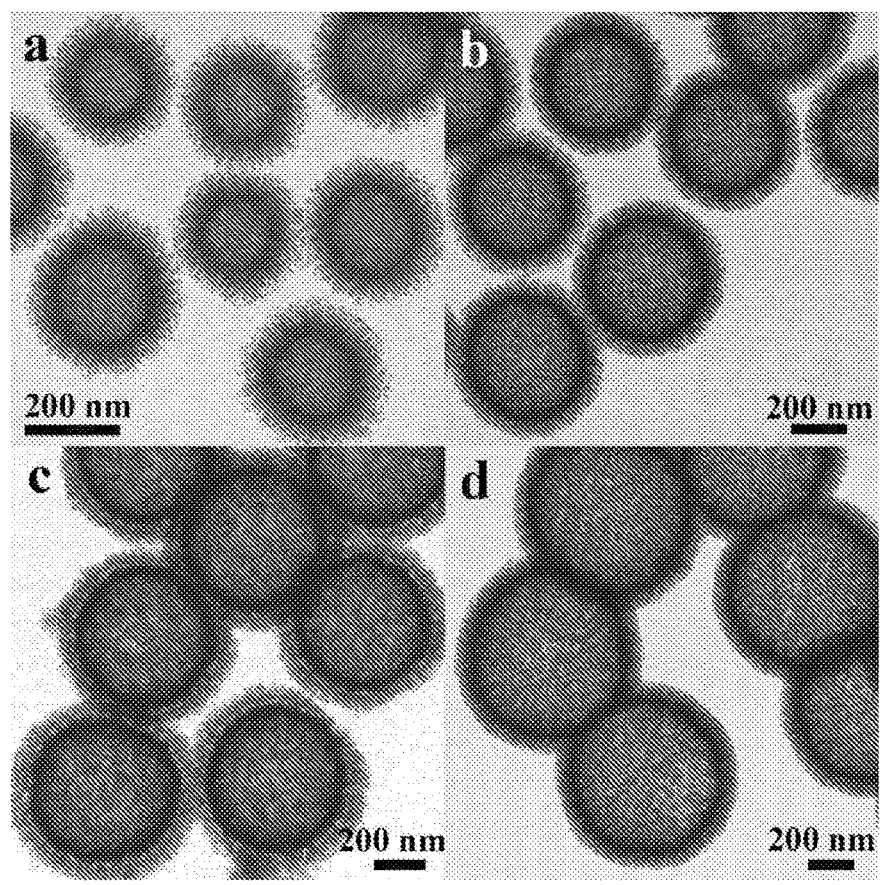
FIG. 24 shows (a) TEM images of MSHS-RS particles made using resorcinol 0.15 g with particle diameter of 307±18 nm, (b) resorcinol 0.30 g particles with particle diameter of 564±20 nm, (c) resorcinol 0.45 g particles with particle diameter of 704±25 nm and (d) resorcinol 0.60 g particles with particle diameter of 837±35 nm (diameter measured from 20 particles), as described in example 8.
Figure 25:
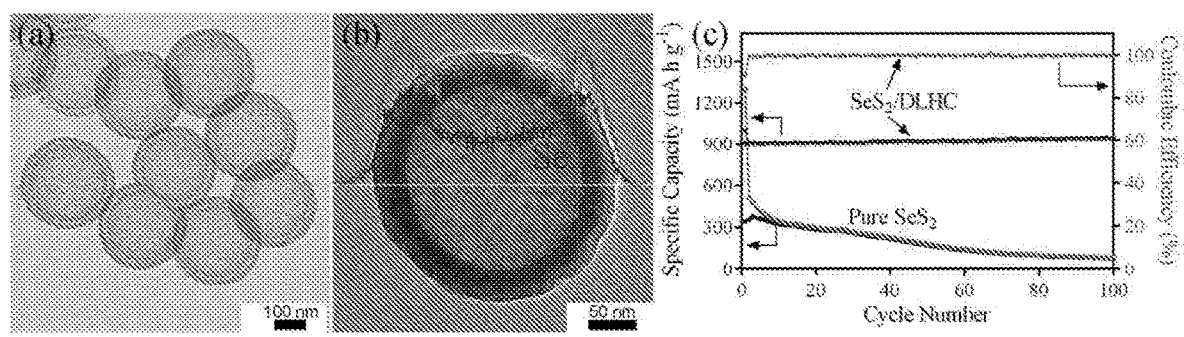
FIG. 25 shows TEM image of (a) as-prepared carbon particles and (b) SeS$_2$/carbon composite (inset: line scanning EDX), and (c) cycling performance of pure SeS2 and SeS$_2$/carbon composite at 200 mA/g.

To demonstrate delivery efficiency of the silica particles with antimicrobial agents, lysozyme was immobilized in these silica hollow spheres. As shown in FIG. 23a, due to the limited external surface area provided for lysozyme adsorption, MSHS-SS particles show the lowest loading capacity of only 61 µg·mg$^{-1}$ (µg lysozyme per mg of silica). In contrast, MSHS-RS particles exhibit the highest loading capacity of 270 µg·mg$^{-1}$, which is two times of that achieved by MSHS-RS-B particles (135 µg·mg$^{-1}$). This is attributed to the increase of mesopore volume from 0.117 cm$^3$·g$^{-1}$ (MSHS-RS-B) to 0.229 cm$^3$·g$^{-1}$ (MSHS-RS). The surface zeta potential of silica hollow spheres before and after lysozyme loading was characterized in 10 mM phosphate buffer solution (PBS). After lysozyme loading, zeta potential of MSHS-SS particles changes dramatically from −29 mV to −3 mV, indicating the positive charged lysozyme is adsorbed on the external surface. However, for MSHS-RS-B and MSHS-RS particles, their surface charge change from −19 mV and −18 mV to −8 mV and −6 mV, respectively. This suggests that lysozyme molecules are typically immobilized into the mesopores of the MSHS-RS-B and MSHS-RS particles, resulting in limited neutralization of surface charge.

Example 6: Lysozyme Release

Lysozyme release behaviour from the silica particles was examined under the condition with fixed initial lysozyme concentration (270 µg·mL-1) in PBS. MSHS-SS particles exhibit a boost release of lysozyme with more than 85% released within 18 h. Compared to these smooth particles, MSHS-RS-B particles show a relatively slower release rate with around 75% of lysozyme released after 24 h. MSHS-RS particles exhibit the most sustained release profile among three particles, with only 74% of lysozyme released at 72 h. However, MSHS-RS with a relatively large pore size are supposed to have a fast release profile. The retarded release of protein molecules from MSHS-RS may result from the enhanced surface hydrophobicity induced by the surface roughness and accessible inner cavity.

Example 7: Antibacterial Activity of Formulated Lysozyme

The in vitro antibacterial activity of free lysozyme and lysozyme loaded silica particles formulated using the above procedure were compared by the optical density (OD) measurement. $E.\ coli$ (5×10$^6$ CFU·mL$^{-1}$) was incubated with various concentrations of lysozyme and corresponding lysozyme loaded silica particles for 24 h. Across all samples dose dependent antibacterial performance was observed wherein higher concentrations/loadings of lysozyme resulted in greater antibacterial activity. Lysozyme formulated into the silica particles showed higher activity compared to free lysozyme at the same lysozyme concentration and this effect is more significant at lysozyme concentration above 500 µg·mL$^{-1}$. Rough silica particles exhibit enhanced antibacterial activity towards $E.\ coli$ relative to free lysozyme and MSHS-SS particles especially for MSHS-RS particles, showing a minimum inhibitory concentration (MIC) value of 700 µg·mL$^{-1}$ for the latter. In contrast, the MIC of free lysozyme towards $E.\ coli$ cannot be achieved even at the concentration as high as 2 mg·mL$^{-1}$.

To further demonstrate the advantages of the silica particles as lysozyme carriers, the long-term bacterial inhibition was tested via bacteria kinetic tests under batch culture. The time dependent bacterial growth at lysozyme concentration of 700 µg·mL$^{-1}$ was monitored for 3 days (FIG. 2b). LB-agar plate assay was employed to examine the bacterial viability after 3-day treatment. It was observed that MSHS-RS particles maintained 100% bacterial inhibition throughout the three day test. This three-day inhibition result is comparable to the performance of silver loaded silica nanoparticles at 80 µg·mL$^{-1}$ as demonstrated by the bacterial kinetic assay. In contrast, time dependent bacterial growth as evidenced by the increase of OD value is observed for MSHS-SS, MSHS-RS-B and free lysozyme formulations. No viable colonies can be observed on the agar plates for bacteria treated with lysozyme loaded MSHS-RS particles showing strong bactericidal activity of the silica particles as opposed to the other samples. The long-term bacterial inhibition property should be attributed to two advantages provided by the design of the silica particles: 1) enhanced adhesion to bacterial surface enabled by the surface roughness which results in efficient, targeted delivery of lysozyme and enriched local concentration of lysozyme on the bacterial surface, and 2) prolonged antimicrobial activity achieved by the sustained release of lysozyme from MSHS-RS particles. However, due to relatively weak particle-bacteria interaction and fast lysozyme release, MSHS-SS and MSHS-RS-B fail to control the bacterial growth with inadequate lysozyme concentration delivered efficiently towards the bacterial surface.

Example 8: Formulation of Particles with Ivermectin

Ivermectin was loaded using rotary evaporation into the MSHS-RS, MSHS-SS and MSHS-RS particles functionalised with hydrophobic octadecyl moieties to render the surface more hydrophobic. Thermogravimetric analysis (TGA) showed an ivermectin loading level in the silica particles of around 23 wt. %, which is in accordance with the feeding ratio of ivermectin to silica nanoparticles (1:3).

To investigate the UV protection properties of the silica particles toward ivermectin these nano-formulations as well as pure (free) ivermectin were treated under UV irradiation for 3 h. The samples before and after UV irradiation were analysed using high performance liquid chromatography (HPLC) to identify their compositions. Free ivermectin was fully degraded after 3 h of irradiation. The ivermectin loaded into MSHS-SS particles showed significant degradation of ivermectin. This may result from the fact that ivermectin is only partially loaded into the internal cavity of the MSHS-SS particles, resulting in only partial protection. In contrast, HPLC analysis ivermectin formulations using MSHS-RS particles and hydrophobically modified MSHS-RS particles showed no significant degradation of ivermectin, indicating the ivermectin composition was well protected by the nanoparticles.

Example 9: Varying the Size of MSHS-RS Particles

MSHS-RS nanoparticles with different particle size were synthesized by varying the amount of resorcinol and formaldehyde in the first addition. By increasing the resorcinol and formaldehyde amount, larger RF polymer nanospheres can be formed acting as the core, leading to an increase in MSHS-RS particle diameters from 307 nm (resorcinol 0.15 g) to 564 nm (resorcinol 0.3 g), to 704 nm (resorcinol 0.45 g) and to 837 nm (resorcinol 0.6 g). As shown in FIG. 24, the resulting MSHS-RS particles in varied sizes still maintain the spiky surface topography. Nitrogen sorption results showed that the resulting particles has mesoporous structures with pore size around 10-20 nm. As the particle size enlarges, the surface area and pore volume of the MSHS-RS particles increased as shown in Table 1.

TABLE 1

Nitrogen sorption determined physicochemical properties for MSHS-RS particles.

| Samples | $S_{BET}$ ($m^2$/g) | $V_{Total}$ ($cm^3$/g) | $d_{pore}$ (nm) |
|---|---|---|---|
| resorcinol 0.15 g | 178 | 0.434 | 12.1 |
| resorcinol 0.30 g | 227 | 0.548 | 16.5 |
| resorcinol 0.45 g | 268 | 0.665 | 16.5 |
| resorcinol 0.60 g | 275 | 0.831 | 16.5 |

Example 10: Formulation with p-DNA

MSHS-RS and MSHS-SS particles with a diameter of around 350 nm were synthesized. Highly negative charges are a well-recognised feature of p-DNA molecules, thus cationic functional groups were introduced onto the silica particles to enhance the electrostatic attraction between p-DNA and the silica by coating the silica particles with polyethylenimine (PEI). After PEI modification, the silica particles still maintain their spiky topography. Nitrogen sorption results showed that PEI modified MSHS-RS particles exhibited mesoporous structures with pore size around 11 nm. The pore size can be enlarged to 16 and 19 nm by hydrothermal treatment at temperatures of 100 and 130° C. respectively, and the hydrothermal treatment at 150° C. can further enlarge the pore size with a wide distribution from 20 to 80 nm. The zeta potential of these the MSHS-RS particles changes from negative (~−20 to −30 mV) to positive (~+15 mV) after PEI modification, indicating the successful introduction of PEI groups on the silica particle surface.

Nanodrop measurement and a gel retardation assays were performed to assess binding capacity with the plasmid pcDNA3-EGFP that encodes for Enhanced. Green Fluorescent Protein (EGFP). PEI modified MSHS-RS particles display much higher pcDNA3-EGFP binding capacity (29.7 ng/μg) than the PEI-modified MSHS-SS particles (14.7 ng/μg). To be noted, MSHS-RS particles that has undergone hydrothermal treatment showed even larger p-DNA loading capacity compared with the MSHS-RS particles without hydrothermal treatment due the enlarged pore size and pore volume. In the gel retardation assay, a constant amount of pcDNA3-EGFP (0.5 μg) was mixed with various amounts of PEI modified silica particles from 0 to 80 μg.

Example 11: Formulation of Battery Electrodes and Battery Cells $SeS_2$ was impregnated into carbon particles in accordance with the present invention by a simple melt-impregnation to obtain the $SeS_2$/carbon composite. A transmission electron microscope (TEM) image of $SeS_2$/carbon is shown in FIG. 25*b*. It is clearly seen that the contrast is higher in the interlayer space than in the hollow cavity. This difference is not observed in the TEM image of the bare particles (FIG. 25*a*), indicating that $SeS_2$ predominately locates in the interlayer space between the two carbon shells rather than in the cavity. The underlying reason is possibly due to a higher capillary force in a smaller nano-space to attract $SeS_2$, which explains our observation in trial experiments that single-layered carbon hollow spheres with microporous walls cannot load S/$SeS_2$ in their cavity. Therefore, the choice of multi-layered hollow carbon such as the carbon of the present invention is essential in our design. The electrochemical evaluation suggests that the $SeS_2$/carbon composite exhibits an excellent cycling stability, high specific capacity and high Coulombic efficiency (FIG. 25*c*). A battery was constructed using the $SeS_2$/carbon particles as the basis of the cathode and lithium metal was used as the anode. After 100 cycles, the reversible capacity still remains at 930 mAh/g with no capacity decay at 200 mA/g. The Coulombic efficiency levels off at 99.5% from the $2^{nd}$ cycle. For comparison, pure $SeS_2$ shows a much inferior cycling performance. The capacity decreases continuously throughout the cycling such that after 100 cycles a low capacity of 75 mAh/g is observed. These proof-of-concept results highlight that carbon spheres of the present invention are excellent hosts for $SeS_2$ and the $SeS_2$/carbon composites are promising electrode materials for next-generation Li—$SeS_x$ batteries.

In the present specification and claims (if any), the word 'comprising' and its derivatives including 'comprises' and 'comprise' include each of the stated integers but does not exclude the inclusion of one or more further integers.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims (if any) appropriately interpreted by those skilled in the art.

The invention claimed is:

1. A particulate material comprising rough mesoporous hollow silica nanoparticles having a size from 100 nm to 3000 nm; wherein the rough mesoporous hollow silica nanoparticles comprise a mesoporous shell that has an external surface that has projections thereon; wherein the projections have lengths ranging from 5 nm to 1000 nm; and wherein the projections are strands or cylinders or fibres or rod-like projections spaced apart from each other and extending outwardly from the mesoporous shell of the rough mesoporous hollow silica nanoparticles, wherein the rough mesoporous hollow silica nanoparticles are synthesized by a process comprising the steps of
I) forming a sacrificial particle from a reaction mixture, the sacrificial particle being formed from a carbon-based material,
II) adding a precursor of silica to the reaction mixture to form a shell containing silica around the sacrificial particle, the shell having outgrowths of material extending therefrom with carbon-based material being formed from the reaction mixture between the outgrowths of material, and
III) subsequently removing the carbon-based material.

2. The particulate material as claimed in claim 1 wherein the carbon-based material comprises a polymer formed by the reaction of two or more monomers or polymer precursors and the outgrowths of material comprise silica.

3. The particulate material as claimed in claim 1 wherein the silica precursor material forms silica at a faster rate than the formation of the carbon containing material such that a shell of silica is first deposited on the surface of the sacrificial particles and once the shell of silica has been formed, the precursors to the carbon-based material start forming additional carbon-based material on the shell whereby growth of carbon-based material competes with growth of silica species on the shell of silica, which results in outgrowths of silica and outgrowths of the carbon-based material.

4. The particulate material as claimed in claim 3 wherein the growth of carbon-based material competes with growth of silica species on the shell of silica and results in radially extending outgrowths of silica and outgrowths of the carbon-based material to form a layer of rod-like silica projections and carbon-based material between the rod-like silica projections, and subsequently removing the carbon based material.

5. The particulate material as claimed in claim 4 wherein the silica species in the reaction mixture are consumed and remaining precursors to the carbon-based material further deposit or react to form an outermost layer of carbon-based material, and the carbon based material is subsequently removed.

6. The particulate material as claimed in claim 1 wherein the carbon-based material is removed by calcination, or by using a solvent.

7. The particulate material as claimed in claim 1 wherein the carbon-based material is formed from a reaction mixture that comprises resorcinol-formaldehyde, aminophenol-formaldehyde or dopamine and the sacrificial particles are formed under Stöber synthesis conditions of ammonia aqueous solution, deionized water and ethanol with a pH=11.5 at room temperature, and the silica precursor comprises tetraethyl orthosilicate (TEOS), tetrapropyl orthosilicate (TPOS) or tetrabutoxysilane (TBOS), or tetramethyl orthosilicate (TMOS).

8. The particulate material of claim 7 wherein the carbon-based material is formed from a reaction mixture that comprises resorcinol-formaldehyde and the silica precursor comprises TEOS, and a weight ratio of TEOS to resorcinol and formaldehyde is 1:0.71 and 1:0.81, respectively.

9. The particulate material of claim 1 wherein the silica precursor is added to the reaction mixture after the sacrificial particle has formed and a further addition of precursors for the carbon-based material is subsequently made at a later time.

10. The particulate material of claim 1 wherein one or more of the precursors for the carbon-based material in the reaction mixture are fully consumed in forming the sacrificial particle, following which the silica precursor for the shell material is added and further of the precursors for the carbon-based material are added a predetermined period after addition of the shell material precursor.

11. The particulate material of claim 1 wherein the silica precursor forms silica at a significantly faster rate than the precursors for the carbon-based material form the carbon based material.

12. The particulate material as claimed in claim 1, wherein the length of the projections range from 5 nm to 500 nm.

13. The particulate material as claimed in claim 1, wherein the rough mesoporous hollow silica nanoparticles have a hollow core defined by the mesoporous shell.

14. The particulate material as claimed in claim 1, wherein the mesoporous shell has a pore structure that includes pores in the range of from 2 nm to 20 nm.

15. The particulate material as claimed in claim 1, wherein the mesoporous shell that surrounds the hollow core has a thickness of from 10 nm to 100 nm.

16. The particulate material as claimed in claim 1, wherein a diameter of the projections ranges from 2 nm up to 100 nm.

17. The particulate material as claimed in claim 1, wherein a specific surface area of the nanoparticles ranges from 100 $m^2/g$ to 1000 $m^2/g$.

18. A composition comprising particulate material as claimed in claim 1; wherein the rough mesoporous hollow silica nanoparticles have one or more active molecules therein or thereon.

19. The composition as claimed in claim 18, wherein the one or more active molecules are present in spaces between the projections.

20. A composition for providing sustained release of a compound, the composition comprising the particulate material as claimed in claim 1, wherein the rough mesoporous hollow silica nanoparticles have the compound taken up therein or thereon.

21. The composition as claimed in claim 20, wherein the compound comprises a hydrophobic protein, a hydrophobic drug, or a therapeutic agent.

22. The composition as claimed in claim 21, wherein the therapeutic agent is an antibiotic.

23. A composition comprising the particulate material as claimed in claim 1, wherein the rough mesoporous hollow silica nanoparticles are at least partially coated with nucleic acid.

24. The composition as claimed in claim 23, wherein the nucleic acid is selected from one or more of plasmid DNA (p-DNA) and messenger RNA (mRNA).

25. The particulate material as claimed in claim 1, wherein a specific surface area of the nanoparticles ranges from 150 $m^2/g$ to 1000 $m^2/g$.

26. The particulate material as claimed in claim 1, wherein a specific surface area of the nanoparticles ranges from 175 $m^2/g$ to 1000 $m^2/g$.

27. The composition as claimed in claim 20, wherein the compound comprises a hydrophobic compound.

28. The composition as claimed in claim 20, wherein the compound comprises an insecticide or a pesticide.

29. The composition as claimed in claim 28, wherein the insecticide or pesticide is selected from the group consisting of Spinosad, pyrethroid, azadirachtin, and pyrethrum.

30. The composition as claimed in claim 20, wherein the compound comprises a hydrophobic dye.

31. The particulate material as claimed in claim 1 wherein the projections have a minimum length of 30 nm, up to a length of 1000 nm.

\* \* \* \* \*